(12) United States Patent
Frieman et al.

(10) Patent No.: US 10,434,116 B2
(45) Date of Patent: Oct. 8, 2019

(54) METHODS OF TREATING CORONAVIRUS INFECTION

(71) Applicants: Matthew Frieman, Hunt Valley, MD (US); Peter B. Jarhling, Gaithersburg, MD (US); Lisa E. Hensley, Frederick, MD (US)

(72) Inventors: Matthew Frieman, Hunt Valley, MD (US); Peter B. Jarhling, Gaithersburg, MD (US); Lisa E. Hensley, Frederick, MD (US)

(73) Assignees: University of Maryland, Baltimore, Baltimore, MD (US); United States Government as represented by the Secretary, Department of Health and Human Services, Bethesda, MD (US)

(*) Notice: Subject to any disclaimer, the term of this patent is extended or adjusted under 35 U.S.C. 154(b) by 0 days.

(21) Appl. No.: 15/302,915

(22) PCT Filed: Apr. 7, 2015

(86) PCT No.: PCT/US2015/024631
§ 371 (c)(1),
(2) Date: Oct. 7, 2016

(87) PCT Pub. No.: WO2015/157223
PCT Pub. Date: Oct. 15, 2015

(65) Prior Publication Data
US 2017/0027975 A1    Feb. 2, 2017

Related U.S. Application Data

(60) Provisional application No. 61/976,031, filed on Apr. 7, 2014.

(51) Int. Cl.
| | |
|---|---|
| *A61K 31/7068* | (2006.01) |
| *A61K 31/506* | (2006.01) |
| *A61K 31/5415* | (2006.01) |
| *A61K 38/21* | (2006.01) |
| *A61K 45/06* | (2006.01) |
| *A61K 31/13* | (2006.01) |
| *A61K 31/138* | (2006.01) |
| *A61K 31/4706* | (2006.01) |
| *A61K 31/522* | (2006.01) |
| *A61K 31/662* | (2006.01) |
| *A61K 31/675* | (2006.01) |
| *A61K 31/7012* | (2006.01) |
| *A61K 31/7056* | (2006.01) |
| *A61K 31/7072* | (2006.01) |
| *A61K 31/7125* | (2006.01) |
| *A61K 31/435* | (2006.01) |
| *A61K 31/46* | (2006.01) |
| *A61K 31/4709* | (2006.01) |
| *A61K 31/496* | (2006.01) |
| *A61K 31/55* | (2006.01) |

(52) U.S. Cl.
CPC .......... *A61K 31/7068* (2013.01); *A61K 31/13* (2013.01); *A61K 31/138* (2013.01); *A61K 31/435* (2013.01); *A61K 31/46* (2013.01); *A61K 31/4706* (2013.01); *A61K 31/4709* (2013.01); *A61K 31/496* (2013.01); *A61K 31/506* (2013.01); *A61K 31/522* (2013.01); *A61K 31/5415* (2013.01); *A61K 31/55* (2013.01); *A61K 31/662* (2013.01); *A61K 31/675* (2013.01); *A61K 31/7012* (2013.01); *A61K 31/7056* (2013.01); *A61K 31/7072* (2013.01); *A61K 31/7125* (2013.01); *A61K 38/21* (2013.01); *A61K 38/212* (2013.01); *A61K 38/215* (2013.01); *A61K 38/217* (2013.01); *A61K 45/06* (2013.01)

(58) Field of Classification Search
CPC .... A61K 31/506; A61K 31/13; A61K 31/138; A61K 31/46; A61K 45/06; A61K 31/496; A61K 31/4706; A61K 31/4709; A61K 31/7068; A61K 31/435; A61K 38/21; A61K 31/522; A61K 31/5415; A61K 31/55; A61K 31/662; A61K 31/675; A61K 31/7012; A61K 31/7125; A61K 38/212; A61K 38/215; A61K 38/217
See application file for complete search history.

(56) References Cited

PUBLICATIONS

Dyall et al. Repurposing of clinically developed drugs for treatment of Middle East respiratory syndrome coronavirus infection. Antimicrob Agents Chemother. Aug. 2014;58(8):4885-93. doi: 10.1128/AAC.03036-14. Epub May 19, 2014.*
Sisk et al. Coronavirus S protein-induced fusion is blocked prior to hemifusion by Abl kinase inhibitors. J Gen Virol. May 2018;99(5):619-630. doi: 10.1099/jgv.0.001047. Epub Mar. 20, 2018.*
WHO. 2003. Summary of probable SARS cases with onset of illness from Nov. 1, 2002 to Jul. 31, 2003. www.who.int/csr/sars/country/table2004_04_21/en/index.html.
Zaki et al, 2012. Isolation of a Novel Coronavirus from a Man with Pneumonia in Saudi Arabia. N. Engl. J. Med. 367:1814-1820.
Abdallat et al., 2013. State of knowledge and data gaps of Middle East respiratory syndrome coronavirus (MERS-CoV) in humans. PLoS Curr. 5:doi: 10.1371/currents.outbreaks.0bf719e352e7478f8ad85fa30127ddb8 pp. 1-31.
Alagaili et al., 2014. Middle East Respiratory Syndrome Coronavirus Infection in Dromedary Camels in Saudi Arabia. mBio 5:e00884-14.
Meyer et al., 2014. Antibodies against MERS Coronavirus in Dromedaries, United Arab Emirates, 2003 and 2013. Emerg. Infect. Dis. 20:552-559.
Memish et al., 2013. Middle East Respiratory Syndrome Coronavirus in Bats, Saudi Arabia. Emerg. Infect. Dis. 19:1819-1823.

(Continued)

*Primary Examiner* — Gregory S Emch
(74) *Attorney, Agent, or Firm* — Benjamin Aaron Adler

(57) ABSTRACT

The present invention provides methods for treating a coronavirus infection. For example, treatment may be effected by administering a neurotransmitter inhibitor, a signaling kinase inhibitor, an estrogen receptor inhibitor, a DNA metabolism inhibitor or an anti-parasitic agent. Also provided are methods for treating a coronavirus infection in which an anti-viral drug also is administered during any of the described methods.

7 Claims, 15 Drawing Sheets

(56) References Cited

PUBLICATIONS

Ithete et al., 2013. Close Relative of Human Middle East Respiratory Syndrome Coronavirus in Bat, South Africa. Emerg. In 5 fect. Dis. 19:1697-1699.
Annan et al., 2013. Human Betacoronavirus 2c EMC/2012-related Viruses in Bats, Ghana and Europe. Emerg. Infect. Dis. 19:456-459.
Perera et al., 2013. Euro Surveill. 2013;18(36):pii=20574. Available online: http://www.eurosurveillance.org/ViewArticle.aspx?ArticleId=20574.
Zhao et al., 2014. Rapid generation of a mouse model for Middle East respiratory syndrome. Proc. Natl. Acad. Sci. U. S. A. 111:4970-4975.
Falzarano et al., 2013. Inhibition of novel b coronavirus replication by a combination of interferon-a2b and ribavirin. Sci. Rep. 3:1686.
Falzarano et al., 2013. Interferon-α1b and ribavirin treatment improves outcome in MERS-CoV-infected rhesus macaques. Nat Med. 19:1313-1317.
Al-Tawfiq et al., 2014. Mass gathering medicine: 2014 Hajj and Umra preparation as a leading example. Int. J. Infect. Dis. pii:S1201-9712(13)00376-7.
Hart et al., 2014. Interferon-b and mycophenolic acid are potent inhibitors of Middle East respiratory syndrome coronavirus in cell-based assays. J. Gen. Virol. 95: 571-577.
Roberts et al., 2007. A Mouse-Adapted SARS-Coronavirus Causes Disease and Mortality in BALB/c Mice. PLoS Pathog. 3:e5.
De Groot et al., 2013. Middle East Respiratory Syndrome Coronavirus (MERS-CoV): Announcement of the Coronavirus Study Group. J. Virol. 87:7790-7792.
Joki-Korpela et al., 2001. Entry of Human Parechovirus 1. J. Virol. 75:1958-1967.
Madrid et al., 2013. A Systematic Screen of FDA-Approved Drugs for Inhibitors of Biological Threat Agents. PLoS One 8:e60579.
Garcia et al., 2012. Productive Replication of Ebola Virus Is Regulated by the c-Abl1 Tyrosine Kinase. Sci. Transl. Med. 4:123ra24. doi:10.1126/scitranslmed.3003500.
Lehar et al., 2009. Synergistic drug combinations improve therapeutic selectivity. Nat. Biotechnol. 27:659-666.
Bosch et al., 2008. Cathepsin L Functionally Cleaves the Severe Acute Respiratory Syndrome Coronavirus Class I Fusion Protein Upstream of Rather than Adjacent to the Fusion Peptide. J. Virol. 82:8887-8890.
Chu et al. 2004. Infectious Entry of West Nile Virus Occurs through a Clathrin-Mediated Endocytic Pathway. J. Virol. 78:10543-10555.
Nawa et al., 2003. Interference in Japanese encephalitis virus infection of Vero cells by a cationic amphiphilic drug, chlorpromazine. J. Gen. Virol. 84:1737-1747.
Pho et al., 2000. JC Virus Enters Human Glial Cells by Clathrin-Dependent Receptor-Mediated Endocytosis. J. Virol. 74:2288-2292.
Coyne et al. 2006. Virus-Induced Abl and Fyn Kinase Signals Permit Coxsackievirus Entry through Epithelial Tight Junctions. Cell 124:119-131.
Reeves et al., 2011. Variola and Monkeypox Viruses Utilize Conserved Mechanisms of Virion Motility and Release That Depend on Abl and Src Family Tyrosine Kinases. J. Virol. 85:21-31.
Shoemaker et al., 2013. Multiple Cationic Amphiphiles Induce a Niemann-Pick C Phenotype and Inhibit Ebola Virus Entry and Infection. PLoS One 8:e56265.
Loga et al. 2007. Chlorpromazine in migraine. Emerg. Med. J. 24:297-300. (doi: 10.1136/emj.2007.047860).

Barnard et al., 2006. Evaluation of immunomodulators, interferons and known in vitro SARS-CoV inhibitors for inhibition of SARS-CoV replication in BALB/c mice. Antivir. Chem. Chemother. 17:275-284.
Koo et al., 2013. Salinomycin induces cell death via inactivation of Stat3 and downregulation of Skp2. Cell Death Dis. 4:e693.
Gupta et al., 2009. Identification of selective inhibitors of cancer stem cells by high-throughput screening. Cell 138:645-659.
Huczynski A., 2012. Polyether ionophores—promising bioactive molecules for cancer therapy. Bioorg. Med. Chem. Lett. 22:7002-7010.
Kuismanen et al., 1985. Effect of Monensin on the Assembly of Uukuniemi Virus in the Golgi Complex. J. Virol. 55:813-822.
Brown et al., 2013. Treatment of MERS-CoV: Decision Support Tool.—CoV v.1.1, Jul. 29, 2013.
De Wilde et al., 2014. Screening of an FDA-Approved Compound Library Identifies Four Small-Molecule Inhibitors of Middle East Respiratory Syndrome Coronavirus Replication in Cell Culture. Antimicrob. Agents Chemother. 58:4875-4884.
Denisova et al, 2012. Obatoclax, Saliphenylhalamide, and Gemcitabine Inhibit Influenza A Virus Infection. Journal of Biological Chemistry 287:35324-35332.
Harmon et al. 2010. Role of Abl Kinase and the Wave2 Signaling Complex in HIV-1 Entry at a Post-Hemifusion Step. PLoS Pathog 6(6): e1000956. doi:10.1371/journal.ppat.1000956.
Johansen et al. 2013. FDA-Approved Selective Estrogen Receptor Modulators Inhibit Ebola Virus Infection. Sci Transl Med. 5(190): 190ra79. (doi:10.1126/scitranslmed.3005471).
Inoue et al. 2007. Clathrin-Dependent Entry of Severe Acute Respiratory Syndrome Coronavirus into Target Cells Expressing ACE2 with the Cytoplasmic Tail Deleted. Journal of Virology, 81: 8722-8729.
American Society of Health-System Pharmacists. 2014. Chlorpromazine. Chlorpromazine hydrochloride. In McEvoy GK (ed), AHFS drug information. American Society of Health-System Pharmacists, Bethesda, MD.
Chan et al., 2013. Broad-spectrum antivirals for the emerging Middle East respiratory syndrome coronavirus. J. Infect. 67:606-616.
Cash P., 1982. Inhibition of La Crosse Virus Replication by Monensin, a Monovalent Ionophore. J. Gen. Virol. 59:193-196.
Chong et al., 2006. Inhibition of La Crosse Virus Replication by Monensin, a Monovalent Ionophore. Nat. Chem. Biol. 2:415-416.
Krizanova et al., 1982. Influence of Chlorpromazine on the Replication of Influenza Virus in Chick Embryo Cells. Acta Virol. 26:209-216.
Lu et al., 2013. Molecular basis of binding between novel human coronavirus MERS-CoV and its receptor CD26. Nature 500:227-231.
McFadden G., 2005. Gleevec casts a pox on poxviruses. Nat. Med. 11:711-712.
Raj et al., 2013. Dipeptidyl peptidase 4 is a functional receptor for the emerging human coronavirus-EMC. Nature 495:251-254.
Reusken et al., 2013. Middle East respiratory syndrome coronavirus neutralising serum antibodies in dromedary camels: a comparative serological study. Lancet Infect. Dis. 13:859-866.
Tolomeo et al., 2009. Tyrosine Kinase Inhibitors for the Treatment of Chronic Myeloid Leukemia. Anticancer Agents Med. Chem. 9:853-863.
Wolf et al., 2009. A Benefit-Risk Assessment of Imatinib in Chronic Myeloid Leukaemia and Gastrointestinal Stromal Tumours. Drug Saf. 32:1001-1015.

* cited by examiner

METHODS OF TREATING CORONAVIRUS INFECTION

CROSS-REFERENCE TO RELATED APPLICATION

This is a national stage application under 35 U.S.C. § 371 of pending international application PCT/US2015/024631, filed Apr. 7, 2015, which claims benefit of priority under 35 U.S.C. § 119(e) of provisional application U.S. Ser. No. 61/976,031, filed Apr. 7, 2014, the entirety of which is hereby incorporated by reference.

FEDERAL FUNDING LEGEND

This invention was made with government support under Grant Number AI095569 awarded by the National Institutes of Health. The government has certain rights in the invention.

BACKGROUND OF THE INVENTION

Field of the Invention

The present invention relates generally to the fields of virology, infectious disease and medicine. More specifically, the invention relates to methods of treating a variety of Coronavirus infections in humans.

Description of the Related Art

Middle East respiratory syndrome coronavirus (MERS-CoV) is an emerging virus, and to date no antiviral or therapeutic has been approved for treating patients. Since September 2012, 206 cases, including 86 deaths, have been attributed to infection with MERS-CoV. Currently, supportive care remains the only available treatment option. As the number of cases continues to rise and the geographic range of the virus increases, there is a growing urgency to develop therapeutic interventions.

Prior to 2002, coronaviruses were not considered to be significant human pathogens. Other human coronaviruses such as HCoV-229E and HCoV-OC43 resulted in only mild respiratory infections in healthy adults. In 2002, however, severe acute respiratory syndrome coronavirus (SARS-CoV) emerged in Guangdong Province, China. This virus rapidly spread to 29 different countries, resulting in 8,273 confirmed cases and 775 (9%) deaths (1). While SARS-CoV predominantly impacted Southeast Asia, with significant outbreaks throughout China, Hong Kong, Taiwan, Singapore, and Vietnam, the virus was carried outside the region. Importation of the virus into Canada resulted in 251 confirmed cases and 44 deaths (1).

In 2012, Middle East respiratory syndrome coronavirus (MERS-CoV), was detected in a patient with severe respiratory disease in Saudi Arabia. To date, 636 laboratory-confirmed cases of MERS-CoV infection have been reported, including 193 deaths, across nine countries. The clinical features of MERS-CoV infection in humans range from asymptomatic to very severe pneumonia with the potential development of acute respiratory distress syndrome, septic shock, and multiorgan failure resulting in death. Since the first case of MERS-CoV infection was reported in September 2012 and the virus was isolated, significant progress has been made toward understanding the epidemiology, ecology, and biology of the virus (2). Several assays for the detection of acute infection with MERS-CoV by real-time reverse transcription (RT)-PCR have been developed and are in widespread use (3). Over 30 whole- or partial-genome sequences from different MERS-CoV-infected patients have been posted to GenBank, and phylogenetic trees have been published (3). Dipeptidyl peptidase 4 (also known as CD26) has been identified as the functional cellular receptor for MERS-CoV (4, 5). Ecological studies have suggested that the virus is of animal origin and is most closely related to coronaviruses found in a number of species of bats, with MERS-CoV viral sequences now found in camels in Saudi Arabia (6-9). Interestingly, a subset of MERS-CoV patients reported close contact with camels. Camels may constitute an intermediate animal host, since camel serum samples collected in 2003 and 2013 had antibodies to MERS-CoV, indicating that MERS-CoV circulates in camels (10-12). The recent development of an animal model for MERS-CoV with adenovirus vectored human DPP4 in mice will now allow for further pathogenesis studies with various MERS-CoV strains (13).

The emergences of both SARS-CoV and MERS-CoV have demonstrated the importance of coronaviruses as emerging human pathogens. In July 2013, the International Severe Acute Respiratory & Emerging Infection Consortium (ISARIC) compiled a list of drugs for treatment of MERS-CoV infection based on experience in treating SARS-CoV infection and pandemic influenza (14). The most promising and clinically available drugs were ribavirin and interferon (IFN) since they demonstrated efficacy in an in vivo model for MERS-CoV infection (15, 16). This combination has failed to demonstrate benefit in the small number of severely ill MERS-CoV patients treated (17). Outside ribavirin and IFN, the ISARIC recommendations had few alternatives for treating clinicians. Recently, mycophenolic acid (MPA) and IFN-β were shown to be highly effective against MERS-CoV infection in vitro. The activity of MPA was specific to MERS-CoV, with little activity observed against SARS-CoV infection (18, 19).

Thus, the prior art is deficient in compositions and methods to treat respiratory syndrome coronaviruses. The present invention fulfills this longstanding need and desire in the art.

SUMMARY OF THE INVENTION

The present invention is directed to a method of treating coronavirus in a subject, comprising the step of administering to the subject a therapeutically effective amount of a neurotransmitter inhibitor.

The present invention is further directed to a method of treating coronavirus in a subject, comprising the step of administering to the subject a therapeutically effective amount of a kinase signaling inhibitor.

The present invention is further directed to a method of treating coronavirus in a subject, comprising the step of administering to the subject a therapeutically effective amount of a estrogen receptor inhibitor, anti-parasitic agent or DNA metabolism inhibitor.

The present invention is further directed to a method for treating Middle East respiratory syndrome coronavirus or severe acute respiratory syndrome coronavirus.

Other and further aspects, features, benefits, and advantages of the present invention will be apparent from the following description of the presently preferred embodiments of the invention given for the purpose of disclosure.

BRIEF DESCRIPTION OF DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 1 shows that 28 compounds showed activity (>50% inhibition) against both viruses, while 33 compounds were only active against MERS-CoV. An additional 102 compound subset was screened against SARS-CoV leading to 6 compounds that were only active against SARS-CoV.

FIG. 2A depicts chemical structures of the compounds. R=Cl (Chloropromazine) and R=CF3 (Triflupromazine). Vero E6 cells were infected with MERs-CoV (left panel) or SARS-CoV (right panel) at an m.o.i. of 0.1 and treated for 48 hours with eight doses of chlorpromazine hydrochloride (FIG. 2B) or triflupromazine hydrochloride (FIG. 2C). Antiviral activity is shown with open circles and cytotoxity is shown with dark squares. IC50 values are indicated. Results are representative of one experiment (mean±SEM; n=2).

FIG. 3A shows the structure of Chloroquine. FIG. 3B shows inhibition of virus growth in Vero cells by Chloroquine for MERS-CoV (FIG. 3B) and SARS-CoV (FIG. 3C). Open circle is % inhibition of virus growth compared to DMSO control and dark square is toxicity as measured by Cell Titer Glo viability assay. EC50 for drug and virus combination is 6.28 µM for MERS-CoV and 6.54 µM for SARS-CoV.

DETAILED DESCRIPTION OF THE INVENTION

Figure 1:
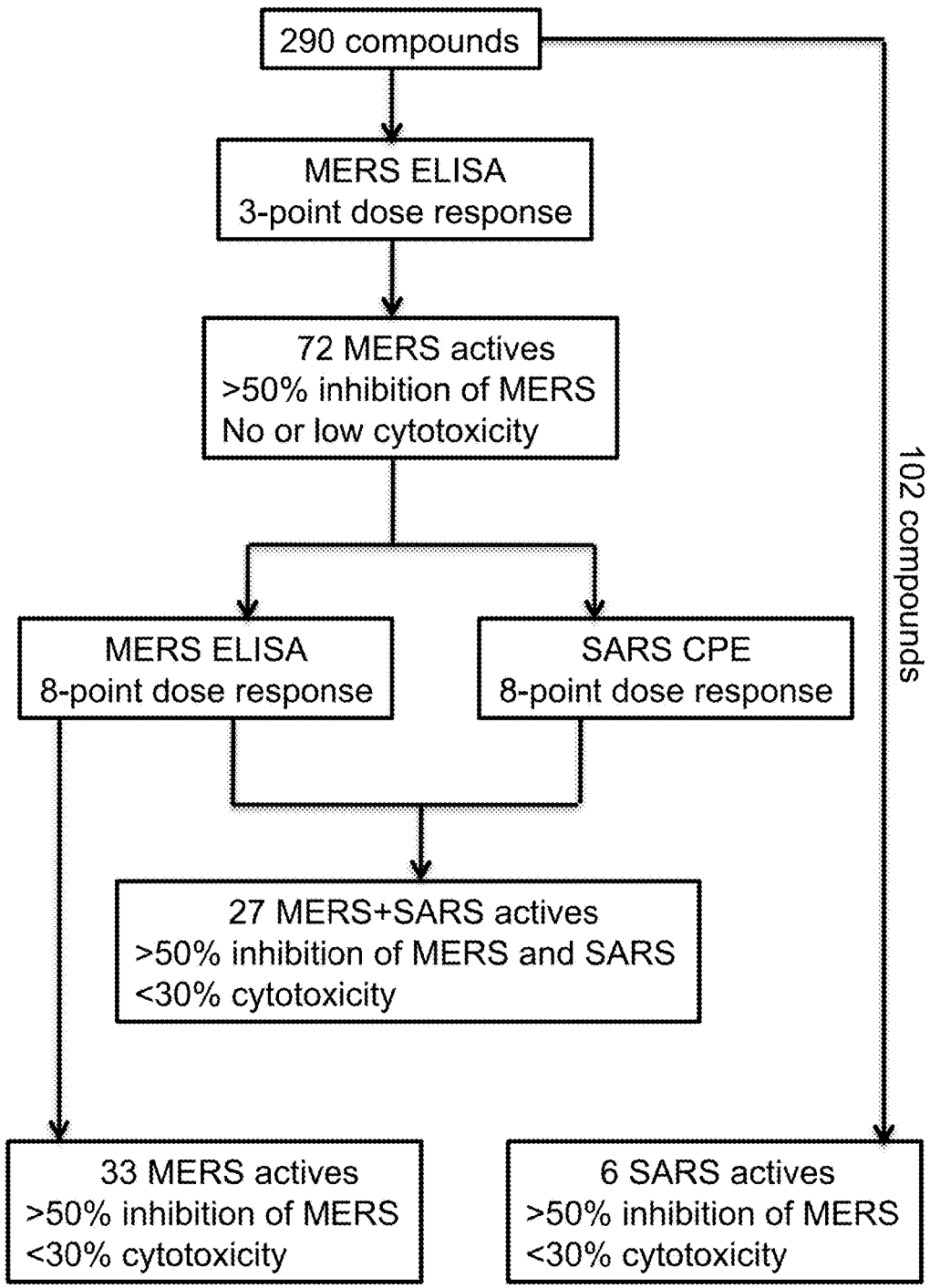
FIG. 1 shows a flowchart of screening procedure. A library of 290 compounds was screened at three doses for activity against MERS-CoV leading to 72 MERS-CoV actives that were subsequently screened against both MERS-CoV and SARS-CoV.

In one embodiment of the present invention, there is provided a method of treating a coronavirus infection in a subject, comprising, the step of administering a therapeutically effective amount of a neurotransmitter inhibitor. Preferably, a representative coronavirus which may be treated using this method include but are not limited to Middle East respiratory syndrome coronavirus or severe acute respiratory syndrome coronavirus. A person having ordinary skill in this art would readily be able to determine useful concentrations of the neurotransmitter inhibitor that would result in a formulation useful to inhibit or treat a coronavirus infection. In one embodiment, the neurotransmitter inhibitor is a dopamine receptor antagonist. Representative examples of useful neurotransmitter inhibitors include but are not limited to chlorpromazine hydrochloride, triflupromazine hydrochloride, clomipramine hydrochloride, thiethylperazine maleate, chlorphenoxamine hydrochloride, promethazine hydrochloride, fluphenazine hydrochloride, thiothixene, fluspirilene, and benztropine mesylate. Preferably, the neurotransmitter inhibitor inhibits viral activity by at least 50%. Typically, the neurotransmitter inhibitor is administered in a concentration range of about 1 mg/kg of the subject's body weight to about 10 mg/kg per day. In one embodiment, the method further comprises the administration of an antiviral drug. Representative examples of useful antiviral drugs include but are not limited to interferons, ribavirin, adefovir, tenofovir, acyclovir, brivudin, cidofovir, fomivirsen, foscarnet, ganciclovir, penciclovir, amantadine, rimantadine, and zanamivir.

In another embodiment of the present invention, there is provided a method of treating a coronavirus infection in a subject, comprising the steps of administering a therapeutically effective amount of a kinase signaling inhibitor. A representative coronavirus which may be treated using this method include but are not limited to Middle East respiratory syndrome coronavirus or severe acute respiratory syndrome coronavirus. Representative examples of useful kinase signalling inhibitors include but are not limited to imatinib mesylate, nilotinib hydrochlorde, and dasatinib. Preferably, the kinase signaling inhibitor inhibits viral activity by at least 50%. Typically, the kinase signaling inhibitor is administered in a concentration range of about 50 mg/kg of the subject's body weight to about 500 mg/kg per day. In a preferred embodiment, the kinase signaling inhibitor inhibits viral RNA production and/or blocks endosomal fusion. In one embodiment, the method further comprises the administration of an antiviral drug. Representative examples of useful antiviral drugs include but are not limited to interferons, ribavirin, adefovir, tenofovir, acyclovir, brivudin, cidofovir, fomivirsen, foscarnet, ganciclovir, penciclovir, amantadine, rimantadine, and zanamivir.

In yet another embodiment of the present invention, there is provided a method of inhibiting or treating a coronavirus infection in a subject, comprising the steps of administering a therapeutically effective amount of an estrogen receptor inhibitor, anti-parasitic agent or DNA metabolism inhibitor. A representative coronavirus which may be treated using this method include but are not limited to Middle East respiratory syndrome coronavirus or severe acute respiratory syndrome coronavirus. Representative examples of useful estrogen receptor inhibitors include but are not limited to toremifene citrate and tamoxifen citrate. Representative examples of useful anti-parasitic agents include but are not limited to chloroquine phosphate, hydroxycloroquine sulfate, mefloquine and amodiaquine dihydrochloride dihydrate. A representative example of a useful DNA metabolism inhibitor includes but is not limited to gemcitabine hydrochloride. Typically, the anti-parasitic drug is administered in a concentration range of about 1 mg/kg of the subject's body weight to about 10 mg/kg per day. In one embodiment, the method further comprises the administration of an antiviral drug. Representative examples of useful antiviral drugs include but are not limited to interferons, ribavirin, adefovir, tenofovir, acyclovir, brivudin, cidofovir, fomivirsen, foscarnet, ganciclovir, penciclovir, amantadine, rimantadine, and zanamivir.

As is well known in the art, the methods of the present invention may be administered to either human or non-human subjects.

As is well known in the art, the methods of the present invention may be administered orally or intravenously.

As is well known in the art, the methods of the present invention may be administered alone or in combination with one or more other commonly used antiviral agents to a subject to treat a particular condition.

As related to the present invention, the term "treating" is defined as prior to prophylactic administration of the compounds in the methods described herein prior to viral infection or inhibiting viral activity after infection has occurred.

The following examples are given for the purpose of illustrating various embodiments of the invention and are not meant to limit the present invention in any fashion.

EXAMPLE 1

Methods

Cell Lines and Virus

Vero E6 cell line (ATCC#1568, Manassas, Va.) was maintained in Dulbecco's modified Eagle's medium (DMEM) plus 10% FBS. The Jordan strain of MERS-CoV (GenBank accession no. KC776174.1, MERS-CoV—Hu/Jordan-N3/2012 [1]), provided by Drs. Kanta Subbarao (National Institutes of Health, Bethesda, Md.) and Gabriel Defang (NAMRU-3) was amplified in Vero E6 cells at a multiplicity of infection (m.o.i.) of 0.01. On day 4 after infection, when the cytopathic effect (CPE) was visible, virus-containing supernatants were collected and clarified by centrifugation. MERS-CoV was titered on Vero E6 cells by plaque assay. All procedures using live MERS-CoV were performed at biosafety level 3 conditions at the Integrated Research Facility (NIAID/NIH), Frederick.

Vero E6 cell line (ATCC#1568, Manassas, Va.) at University of Maryland, Baltimore, was maintained in minimal Eagle's medium (MEM; Corning) supplemented with 10% FBS (SAFC), 1% penicillin/streptomycin (Gemini bio-products) and 1% L-glutamine (Gibco) Mouse adapted SARS-CoV (MA15) has been described (2). SARS-CoV was amplified in Vero E6 cells for 2 days, when the CPE was visible. SARS-CoV containing supernatants were collected and clarified by centrifugation. SARS-CoV was titered on Vero E6 cells by plaque assay. All procedures using live SARS-CoV were performed at biosafety level 3 conditions at the University of Maryland, Baltimore.

Drug Library and Compound Plate Preparation

A library of approved drugs and targeted molecular probes was assembled (Lehár et al., 2009). A subset of 290 compounds was selected for screening against MERS and SARS based on the antiviral activity observed in screens against other RNA viruses (21). For the MERS and SARS screens, compounds were added to compound plates using a Labcyte Echo 555 acoustic compound dispenser. The compounds were shot directly on to 96-well plates from master stock solutions. Following addition of compound, 200 ml of DMEM media was added to plates and plates were frozen at −800 C for a minimum of 24 hours prior to shipment to the investigators. Compound plates were thawed prior to the addition of compound to the infectivity assays described below. Compound plates were thawed prior to the addition of compound to the infectivity assay as described below. For the MERS screen, compounds were plated in 200 mL of media at 4× the final concentrations such that the addition of 50 mL, to assay plates resulted in the appropriate final concentration (200 mL final assay volume). For the SARS screens, drugs were plated in 200 mL of media at 2× the final concentrations such that the addition of 50 mL resulted in the appropriate final concentration (100 mL final assay volume). All drug plates were blinded to those performing the infectivity assays.

Cell-Based ELISA Screen for MERS-CoV Antiviral Agents

Vero E6 cells were seeded at 40,000 cells in 100 μl DMEM plus 10% FBS per well in black, opaque or clear bottom 96 well-plates. Test compounds MPA (# M3536) and ribavirin (# R9644) were obtained from Sigma Aldrich (St. Louis, Mo.), and IFN-β (#11415-1), IFN-α2a (#11101-5), IFN-α2b (#11105-1), IFN-γ (#11500-2), and a recombinant product based on the consensus sequence of the IFN-α subtypes designated as "universal type 1 IFN" (#11200-1) were obtained from PBL (Piscataway, N.J.). After 24 h, three dilutions of test compounds were added to the cells in 50 µl using the 96-well liquidator (Rainin Instrument, Oakland, Calif.). DMSO concentration was kept at 0.05% or lower. The cell plates were transferred into the containment laboratory to add MERS-CoV strain—Hu/Jordan-N3/2012—at an m.o.i. of 0.1 in 50 µl of DMEM plus 10% FBS approximately 1 hour after the addition of the drugs. After 48 h, plates were fixed with 10% neutral-buffered formalin and removed from biocontainment. MERS-CoV was detected with a rabbit polyclonal antibody to the HCoV-EMC/2012 Spike Protein (Sino Biological Inc., Beijing, CN, #40069-RP02) followed by staining with Alexa Fluor® 594 goat anti-rabbit IgG (H+L) antibody (Life Technologies, Grand Island, N.Y.). For Alexa 594 dye, fluorescence was quantified on a plate reader (Infinite® M1000 Pro, Tecan US, Morrisville, N.C.) with excitation wavelength of 590 nm and emission wavelength at 617 nm. Wavelengths of 560-580 nm were used to excite Alexa 594 dye and Emission wavelengths of 590-640 nm were used to detect Alexa 594 fluorescence. Percentage inhibition of treated wells (TREAT) compared to untreated wells (UNTR) was determined using the formula:

% inhibition=[1−(TREAT−Normal)÷(UNTR−Normal)]*100

The signal of treated wells (TREAT) was normalized to uninfected control wells (Normal) and measured (in percent) relative to untreated wells (UNTR). Non-linear regression analysis was performed to calculate IC50s (GraphPad Software, La Jolla Calif.). The MERS-CoV ELISA drug screen was carried out in duplicate for each drug concentration and the assay was repeated with an 8-point dose response for confirmation. Error bars of dose response curves represent the standard deviation of 2 replicates.

Cytotoxicity Assay

To evaluate cytotoxicity of drugs, Vero E6 cells were plated and treated with drugs at the same concentrations used for detection of MERS-CoV replication inhibition as described above for the cell-based MERS-CoV ELISA drug screen, but were not infected with virus. At 48 h after drug addition, plates were analyzed using the CellTiter Glo luminescent cell viability assay kit (Promega, Madison, Wis.), and luminescence was read on the Infinite® M1000 Pro plate reader.

MERS-CoV Virus Yield Reduction Assay

Vero E6 cells were seeded in 12-well plates at 200,000 cells per well. After overnight incubation, the cells were infected in triplicate with MERS-CoV strain—Hu/Jordan-N3/2012 at an m.o.i. of 0.1 and incubated at 37° C. for 1 h with shaking every 15 min. The inoculum was removed, the cells were washed with PBS and fresh media was added containing 10-fold dilutions of IFN-β (10-1000 U ml-1) for 48 and 72 h. Supernatants were collected and titered using the infectivity assay. The assay was carried out with three replicates for each drug concentration and was repeated at least twice for confirmation. Error bars of dose response curves represent the standard deviation of three replicates.

MERS-CoV Infectivity Assay

Vero E6 cells were infected in 8 replicates with 10-fold dilutions of supernatants from the virus yield reduction assay. MERS-CoV was absorbed for 1 h, then removed and replaced with DMEM plus 10% FBS. Cells were incubated at 37° C., 5% CO2 in a humidified environment for 6 days. CPE in wells was scored by fixing and staining the cells with crystal violet. The TCID50 was calculated with Microsoft Excel as described by Reed and Muench [3].

SARS-CoV Cytopathic Effect (CPE) Inhibition Assay

For the SARS-CoV screen, 100 of the 290 drugs were initially screened against SARS-CoV, plus all the hits that blocked MERS-CoV but were not in the initial 100 were also screened against SARS-CoV. Vero E6 cells were seeded into white opaque 96-well plates (Costar) at 1×104 cells per well and cultured overnight at 37° C. Cells were treated with the drugs for 2 hours at 37° C. and then infected with SARS-CoV (MA15) at a m.o.i. of 1. Cells were left cultured at 37 cc for 2 days and then analyzed for cell survival using the CellTiterGlo® luminescent cell viability assay (Promega) according to the manufacturer's instructions and read on a SpectraMax M5 plate reader (Molecular Devices). Media alone controls were used to assess drug toxicity in the absence of SARS-CoV.

MERS-CoV and SARS-CoV Spike Pseudotyping of HIV

Pseudotyped HIV virions that contain MERS-CoV or SARS-CoV Spike protein are produced. The pseudotype system uses the B-lactamase/Vpr chimeric protein technology where cells are pretreated with CCF2 dye as the reporter for B-lactamase release from the endosome into the cytoplasm. Proper entry of the pseudotyped virions leads to fusion of the virion to the endosomal membrane, release of B-lactamase into the cytoplasm and reaction with the CCF2 substrate where it cleaves the β-lactam ring in CCF2, changing its fluorescence emission spectrum from green (520 nm) to blue (447 nm) and thereby allowing fusion to be detected by fluorescence microscopy, flow cytometry, or UV photometry (37). This system is used for detection of receptor binding, trafficking into endosomes and fusion to the endosomal membrane.

The inhibition of virus binding is assayed by Vero E6 cells pre-treated for 2 hours with 50 mm, 10 mM, 2 mM, 0.4 mM or 0 mM of Chlorpromazine, Chloroquine, Imatinib or Nilotinib at 37°. MERS-CoV Spike and SARS-CoV Spike bearing pseudotypes are added at an MOI of 5 and cells were placed at 4° for 1 hour to allow for binding to the cell surface. At 1 hour post-infection, wells are washed with cold PBS to wash off unbound virus and excess drug. Each well is then immediately lysed in protein lysis buffer and the resulting protein extract analyzed on a western blot with anti-p24 antibody specific for the pseudotype. It is estimated that there are 4000-5000 copies of p24 in each pseudotype, much higher than there is Spike, allowing for the detection of pseudotypes at this early stage. Comparison of the amount of p24 protein in treated vs untreated cells determines whether the drugs inhibit virus binding to cells. Additionally, a separate set of wells has cells grown on coverslips. All experimental design are the same however cells are fixed and labeled with a FITC labeled anti-p24 antibody and a Texas Red labeled anti-Rab5 antibody (endosomal marker). The FITC and Texas Red signals are compared to identify if the virions are able to localize to the same endosomes to know whether the drugs alter that localization.

To test the inhibition of virion fusion to the endosomal membrane both the pseudotype system and live virus are used. Vero E6 cells are pre-treated for 2 hours with 50 mm, 10 mM, 2 mM, 0.4 mM or 0 mM of Chloroquine, Chlorpromazine, Imatinib or Nilotinib at 37° C. MERS-CoV and SARS-CoV virus are added at an MOI of 5 and cells are placed at 37° C. for 2 hour to allow for binding and entry of virions into the cells. At 1 hour post-infection, wells are washed with warm PBS to wash off unbound virus and excess drug and replaced with media containing the same concentration of drug used in the pre-treatment. At 12 hours post infection cells are lysed in Trizol and RNA extracted. RNA is then be converted into cDNA and used with 3 a triplex assay by Realtime PCR. Primer set 1 is for the housekeeping gene TRFC (Transferrin receptor), primer set 2 is for the genomic viral RNA with primers for the NSP5 gene, and primer set 3 contains a forward primer containing the leader sequence/TRS overlap sequence and a reverse primer 200 bp into the E ORF (Life Technologies). Each of these primer sets produces a 200 bp PCR product that is readily detected with the 3 different primer sets. Comparisons of treated vs untreated cells are analyzed by comparing Ct values in the Taqman assays. The production of sgRNA signalled that there is release of the virion into the cytoplasm and no effect on transcription.

To identify if viral proteins are being translated and trafficking property, the localization of SARS-CoV and MERS-CoV Spike and M after infection is tracked. Both are glycoproteins that traffic through the ER and Golgi before being packaged into virions and then secreted from the cell. Antibodies to Spike and M from both viruses that work in fixed cells are used. Vero E6 cells are grown on glass coverslips and pre-treated for 2 hours with 50 mm, 10 mM, 2 mM, 0.4 mM or 0 mM of Chloroquine, Chlorpromazine, Imatinib or Nilotinib at 37°. MERS-CoV and SARS-CoV virus are added at an MOI of 5 and cells are placed at 37° for 18 hour to allow replication of the viruses in the cells. The wells are fixed with 4% PFA, removed from the BSL3 and stained with the respective antibodies. After staining the coverslips are imaged on a Zeiss Axioskop confocal microscope to identify if S and M are mislocalized in drug treated cells compared to mock treated cells.

The last step in the Coronavirus replication cycle is virion release from cells. The time of drug addition experiments are used to identify if egress is affected by Chloroquine, Chlorpromazine, Imatinib or Nilotinib. MERS-CoV and SARS-CoV are added at an MOI of 5 and cells are placed at 37° for 1 hour to allow for binding and entry of virions into the cells. At 1 hour post-infection, wells are washed with warm PBS to wash off unbound virus and standard media. At 6 hours post infection cells are treated with 50 mm, 10 mM, 2 mM, 0.4 mM or 0 mM of Chloroquine, Chlorpromazine, Imatinib or Nilotinib and incubated at 37°. At 12, 24, 36 and 48 hours post infection, aliquots of media are removed for titering by plaque assay. Each virus in mock or drug treated cells is compared to identify if there is any effect on virus production in the presence of each drug.

siRNA Knockdown Assays

The role of each targeted Abl kinase inhibitor is identified by using siRNA to knockdown the predicted target of each drug and then infecting with MERS-CoV and SARS-CoV to assess viral replication. This shows whether the intended protein target of each drug is essential for virus viability and proliferation. siRNA pools (Dharmacon) that are targeted to Abl, c-Kit, PDGFR, EPHB4, Lyn and Src are used. Each siRNA pool and a scrambled control is transfected into MRC5 cells in triplicate in a 48 well plate and incubated for 24 hours. At 24 hours, knockdown of each protein is assessed by western blot. Knocked down cells are used for infection experiments where knocked down cells for each gene were infected with MERS-CoV and SARS-CoV at low MOI (0.01 pfu/cell) and high MOI (10 pfu/cell) for 48 hours with aliquots of media taken every 12 hours to assess virus growth. At 48 hours, total protein is extracted from cells to assess knockdown of the targeted protein by western blot. Virus from each timepoint is titered on Vero cells to assess virus growth in cells lacking each protein. This identifies which of the targeted proteins was essential for MERS-CoV and SARS-CoV replication and which drug target is essential for viral replication.

Data Analysis

For the MERS screen a minimum of four replicates were performed on two separate days. For the SARS screen a minimum of two replicates were performed on two separate days. Outlier data points were defined as a value>median+3 s and were excluded from calculations.

Raw phenotype measurements T from each treated well were converted to normalized fractional inhibition I=1−T/V relative to the median V of vehicle-treated wells arranged around the plate. After normalization, average activity values were calculated between replicate measurements at the same treatment doses along with s1, the accompanying standard error estimates. Drug response curves were represented by a logistic sigmoidal function with a maximal effect level (Amax), the concentration at half-maximal activity of the compound (EC50), and a Hill coefficient representing the sigmoidal transition. The fitted curve parameters to calculate the concentration (IC50) at which the drug response reached an absolute inhibition of 50%, limited to the maximum tested concentration for inactive compounds.

Compounds were considered active if the antiviral activity observed was >50% I with no or low corresponding cytoxicity (<30% I).

Animal Model of SARS-CoV

Several mouse models of SARS-CoV have been developed that have various aspects of SARS-CoV disease depending on the virus strain and mouse background used (25, 26). The wildtype human SARS-CoV isolate (Urbani strain) replicates in mice but does not cause disease or lung pathology (25, 26). A mouse-adapted strain of SARS-CoV (called MA15) was produced by serial passage of the Urbani strain in BALB/c mice. MA15 produces a lethal infection in BALB/c mice causing significant lung damage and morbidity by 4 days post infection with death resulting by 5 days post-infection (27) (FIG. 11). When 10-week-old BALB/c mice are intranasally challenged with a 1×105 pfu dose of MA15, it is 100% fatal by 5 days post infection. The MA15 strain in BALB/c mice is a highly lethal reporter of virus infection causing significant lung damage and morbidity.

Using the mouse adapted SARS-CoV strain, MA15 model, Chlorpromazine, Chloroquine, Nilotinib and Imatinib are tested for the ability to protect mice from weight loss, clinical disease and reduce virus titer. The dose of Chlorpromazine given to humans is 5 mg/kg per day, equaling 100 μg/20 g mouse per day. For the Chlorpromazine challenge experiment, daily i.p. injections of 100 mg or 20 mg are given to each group starting at day −1 through day 3 post infection with lung harvests at day 4 post infection. The dose of Chloroquine diphosphate given to humans is 80 mg/kg daily, equaling 1.6 mg/20 g mouse per day. For the Chlorpromazine groups, daily i.p. injections of 1.6 mg or 0.8 mg are given to each group starting with day −1 through day 3 post infection with lung harvests at day 4 post infection. The dose of Nilotinib and Imatinib given is 100 mg/kg/mouse. For all experiments, the drugs are resuspended in water and an i.p. injected water control group was used as a control. Mice are weighed daily and their clinical score recorded evaluating their breathing, activity and coat condition.

Animal Model of MERS-CoV

A mouse model for MERS-CoV was created using an adenovirus vector delivering human DPP4 (hDPP4) into the lungs of mice. Experimentally, mice are intranasally inoculated with the adenovirus/hDPP4 and then 4 days later can be infected with MERS-CoV. This allows for MERS-CoV to replicate in the lung, where it replicates to 105 pfu/g lung by day 2 post infection and produces mild lung pathology in WT mice. This model is used to test for in vivo protection of several drugs, antibodies and vaccines against MERS-CoV.

A transgenic mouse was created that contains the human DPP4 gene in place of the mouse DPP4 gene. Transgenic mice are infected with MERS-CoV at 1×105 pfu/mouse and monitored for the replication of virus. The virus replicates in the lungs of these mice till at least 4 days post infection. These mice had no weight loss or clinical disease however at 4 days post-infection, their lungs displayed moderate inflammation consisting of eosinophils, neutrophils and macrophages. Inflammation was present throughout the lung parenchyma and alveoli. Alveolar spaces displayed infiltrating cells and thickening of the alveolar walls. This is the first transgenic MERS-CoV model to demonstrate replication of MERS-CoV.

Infection of Rhesus macaques with the MERS-CoV (EMC/2012) strain causes mild clinical disease over the first 24 and moderate lung pathology and inflammation (28). MERS-CoV replicates to ~105 TCID 50/g lung in these animals and they develop acute pneumonia by 3 days post infection. The NIH/NIAID Integrated Research Facility (IRF) has developed an intra-tracheal model of MERS-CoV infection that corroborates this data.

Inhibition of SARS-CoV Replication in BALB/c Mice

For the testing of Chloroquine and Chlopromazine, BALB/c mice are pre-treated at day −1 with Chloroquine at 25 mg/mouse, 50 mg/mouse, 100 mg/mouse and 200 mg/mouse. For Chlorpromazine the dosing is 0.3 mg/mouse, 0.9 mg/mouse, 1.8 mg/mouse and 3.6 mg/mouse by i.p. and dosed a single time daily. The mice were infected with 104 pfu/mouse of SARS-CoV (Urbani). Mice are weighed daily and their appearance recorded for clinical signs of disease to detect any enhancement of clinical disease from the drugs. Lungs are harvested from 5 mice per group at 1, 2 and 4 days post infection to analyze the viral load by plaque assay on Vero cells and lung pathology. Histological slides are stained with H&E and scored for pathologic damage. Additionally, lung sections are stained with antibodies to the SARS-CoV Spike protein to localize infected cells during the course of the infection.

The 2 drugs are tested for their ability to reduce viral titer when administered after infection. In these experiments, BALB/c mice are infected as above, however, rather than treating at day −1 with the indicated doses, the most effective dose (1.8 mg/mouse for Chlorpromazine and 100 mg/mouse for Chloroquine) and as used to treat groups of mice, 5 per group, at starting at either day −1, 0, +1, +2 or +3 post infection to test how long after infection the drugs can be given to reduce SARS-CoV virus titer. The analysis is performed to investigate virus titer, lung histology and virus spread.

Inhibition of MERS-CoV Replication in BALB/c Mice

B6/hDPP4 mice are treated at day −1, 0, 1, 2, and 3 days post infection with the mice pre-treated at day −1 with Chloroquine at 25 mg/mouse, 50 mg/mouse, 100 mg/mouse and 200 mg/mouse. For Chlorpromazine the dosing is 0.3 mg/mouse, 0.9 mg/mouse, 1.8 mg/mouse and 3.6 mg/mouse by i.p. and dosed a single time daily. MERS-CoV (Jordan strain) or PBS are intranasally inoculated to each group of mice (5 mice each) at 105 pfu per mouse. For the adenovirus/hDPP4 model, C57B/6 mice are intranasally infected with either an empty adenovirus or Ad/hDPP4 at 108 pfu/mouse. At 4 days post adenovirus infection, the mice are treated with their first dose of drug and then the following day infected with MERS-CoV. Mice in all groups are weighted daily and clinical disease scored as per IACUC protocols.

The lungs are harvested at days 1, 2, 3, 4, and 7 post infection to characterize the infection in the B6/hDPP4 mice as compared to the published Ad/hDPP4 model. Lungs are analyzed for viral load by plaque assay on Vero cells and lung pathology. Histological slides are stained with H&E and scored for pathologic damage. Additionally, lung sections are stained with antibodies to the MERS-CoV Spike protein to localize infected cells during the course of the infection and with antibodies to hDPP4 to analyze expression kinetics of the receptor during infection, especially to identify if alterations in cell types and amounts during infection and response.

Analysis of the Inflammatory Response During MERS-CoV Infection and Treatment

B6/hDPP4 mice are infected with 105 pfu of MERS-CoV (Jordan) and analyzed for the types and quantify of inflammatory cell infiltrates in the lungs during the course of infection, with lungs harvested at days 1, 2, 3, 4 and 7 post infection. The inflammatory cells are profiled with additional subsets of inflammatory cells added as needed including the quantitation of Tregs, Th17, ILCs and macrophage subtypes (including M1 vs M2 macrophages). The normal inflammatory response to infection is compared to that seen during treatment with Chloroquine and Chlorpromazine.

Effectiveness of Protection of Rhesus Macaques from MERS-CoV

There are 3 groups of 3 animals each (1 group received the drug alone, 1 group with only MERS-CoV, and 1 group with drug and MERS-CoV challenge). At 1 day pre-infection, groups of Rhesus are treated with either Chloroquine (80 mg/kg) or Chlorpromazine (5 mg/kg) by oral gavage or intravenously depending on the chosen drug's best route of treatment. At each day after, Rhesus groups receive either 100 mg/kg of drug at twice daily or carrier only by the chosen route. At day 0, Rhesus are intratracheally inoculated with 5×106 PFU of sequence verified MERS-CoV (Jordan isolate). Animals are then evaluated by physical exam and computed tomography. Daily physical exams are taken as well as clinical samples (blood and serum), nasal and throat swabs every other day for 14 days. One animal per group undergoes bronchoalveolar lavage (BAL) at day 0, 2-5, 13, and 14 for plaque assay for viral load, cytokine analysis (by Luminex arrays at IRF), and evaluation of inflammatory cell type present. PET/CT scans are performed daily to monitor lung volume changes during infection and how the drug treatment may effect these changes. Preliminary data demonstrates that between days 1 and 14 post infection they find up to a 10% lung volume loss from the infection by PET/CT analysis. The same analysis is performed for this experiment and compared to the data on virus load, inflammatory infiltrates and blood counts taken daily. At 14 days post infection animals are sacrificed and lungs harvested for analysis.

EXAMPLE 2

Results

Overview of Screening Process

A primary screen of 290 compounds containing both approved drugs and targeted molecular probes was performed with 3 point dose response curves to identify compounds with activity against MERS-CoV using the cell-based ELISA assay (FIG. 1). The analysis of the raw screening data indicated that 72 compounds that were active against MERS-CoV (>50% inhibition) with no or low cytotoxicity (<30% inhibition). In the secondary screen, the 72 compounds were plated at 8 doses for confirmation of antiviral activity against MERS-CoV as well as to determine IC50 values in the MERS-ELISA assay. The 72 compounds were also evaluated for their antiviral activity against SARS-CoV using a cytopathic effect (CPE) inhibition assay. A subset of 102 compounds was independently screened against SARS-CoV to see if there are compounds that are selective for SARS-CoV.

Overview of Drugs Active Against SARS-CoV, MERS-CoV or Both

Analysis of data from all screening activities resulted in a list of 67 compounds that were active against SARS-CoV, MERS-CoV, or both. In summary, six drugs were active against SARS-CoV only, 33 drugs that were active against MERS-CoV only and 28 drugs that were active against both SARS-CoV and MERS-CoV. These drugs were grouped based upon their recognized mechanism of action into thirteen different therapeutic classes that were active against SARS-CoV, MER-CoV or both (Table 1). The high hit rates of 21% (61 out of 290) for MERS-CoV inhibitors and 19.5% (34 out of 174) for SARS-CoV inhibitors can be explained by the fact that the library is enriched for compounds that have shown antiviral activity against other viruses.

TABLE 1

Classes of compounds with activity against MERS-CoV and/or SARS-CoV in vitro

| Mechanism of action | SARS only | MERS only | SARS and MERS | Total |
|---|---|---|---|---|
| anti-bacterial | | 1 | 1 | 2 |
| anti-parasite | | 2 | 4 | 6 |
| neurotransmitter inhibitors | 2 | 3 | 11 | 16 |
| estrogen receptor inhibitors | | 3 | 2 | 5 |
| DNA inhibitors | | 3 | 1 | 4 |
| protein processing inhibitors | | 1 | 3 | 4 |
| signaling kinase inhibitors | 1 | | 2 | 3 |
| cytoskeleton inhibitors | | 8 | | 8 |
| Lipid, sterol metabolism inhibitors | | 2 | 3 | 5 |
| anti-inflammatory | 3 | | | 3 |
| ion channel inhibitors | | 9 | | 9 |
| apoptosis inhibitors | | 1 | | 1 |
| cathepsin inhibitors | | | 1 | 1 |
| Total | 6 | 33 | 28 | 67 |

Pharmaceuticals that inhibit both coronaviruses include neurotransmitter inhibitors, estrogen receptor antagonists, kinase signaling inhibitors; inhibitors of lipid or sterol metabolism, protein processing inhibitors, and inhibitors of DNA synthesis/repair. Anti-parasitics or anti-bacterials were another two classes of pharmaceuticals where function was not obviously linked to coronaviruses, or viruses in general. A cathepsin inhibitor, E-64-D, was found to block both SARS-CoV and MERS-COV. This was less surprising since it is known that cathepsins are important for the fusion step during virus entry of coronaviruses (4).

Interestingly, there are also classes of drugs that seem to inhibit only SARS-CoV or MERS-CoV, but not both. Though a small number of SARS-CoV only inhibitors were identified, they are mostly anti-inflammatories, which interfere with cell signaling associated with the immune reaction to the virus infection. MERS-CoV was specifically blocked by inhibitors of ion transport, of cytoskeleton (specifically tubulin), and apoptosis.

Figure 2A:
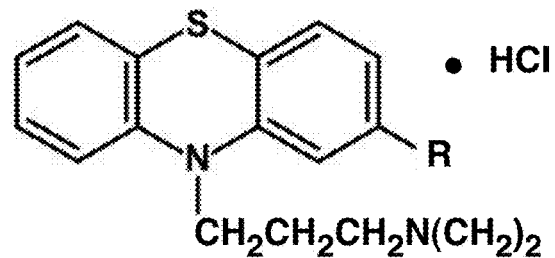
FIGS. 2A-2C show antiviral activity of chlorpromazine hydrochloride and triflupromazine hydrochloride.
Figure 2B:
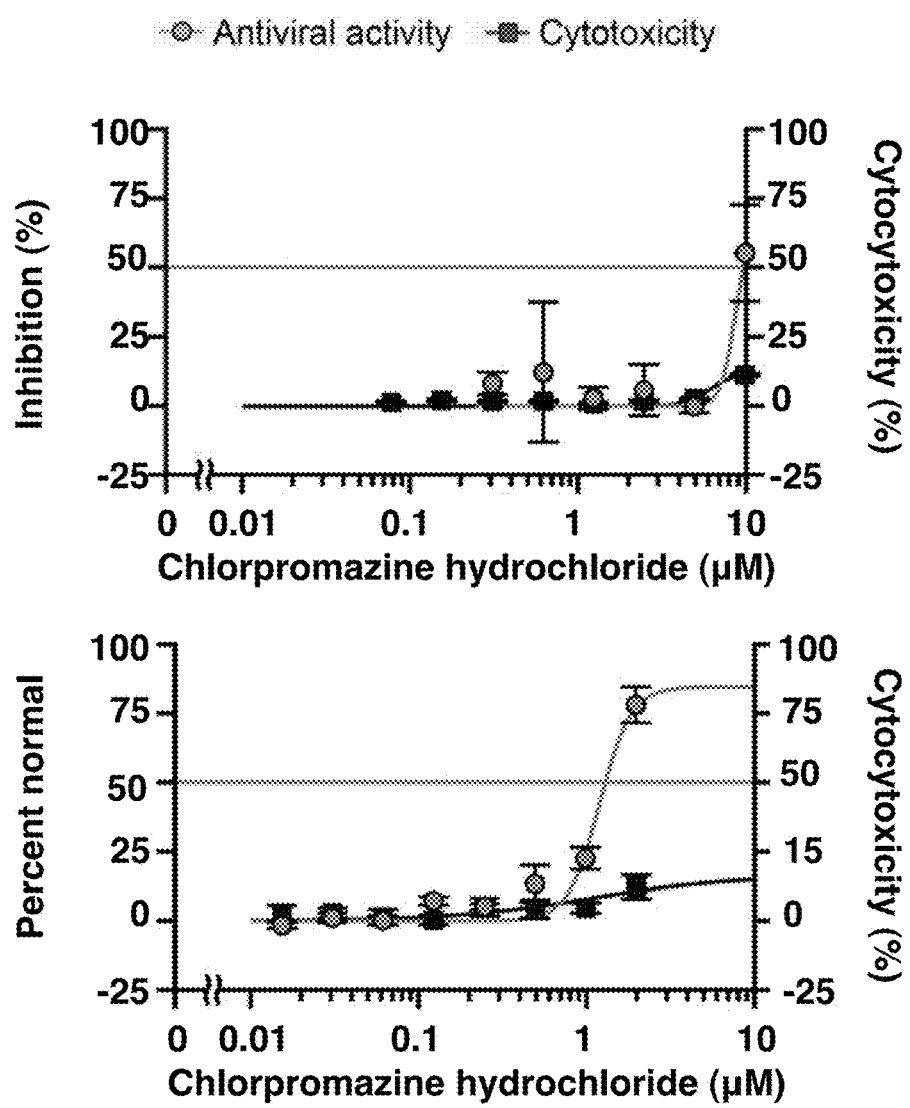
Figure 2C:
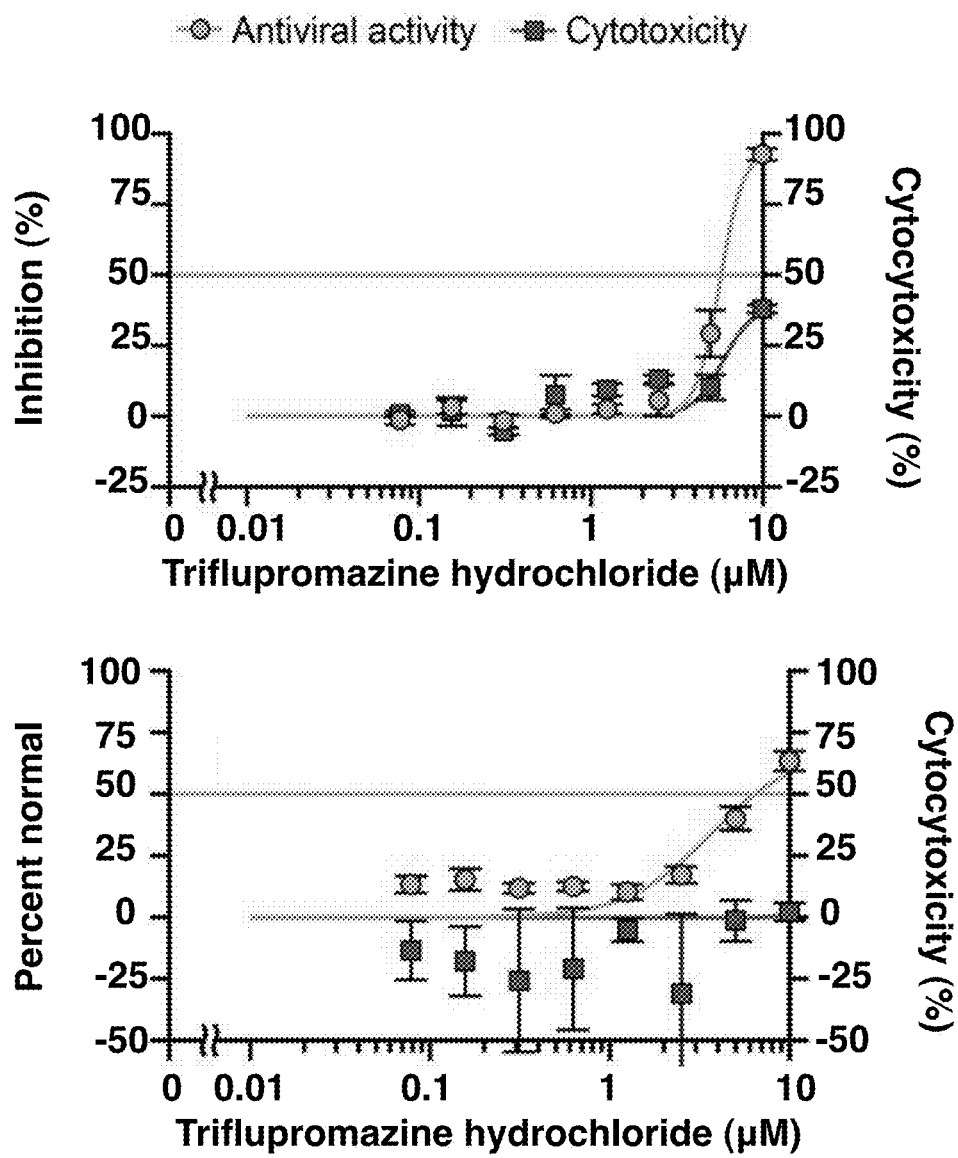

Specific Drugs 28 specific drugs that block both SARS-CoV and MERS-CoV from a primary screen of 290 compounds containing both approved drugs and targeted molecular probes that was performed with 3 point dose response curves to identify compounds with activity against MERS-CoV using the cell-based ELISA assay (Table 2). In total, 16 neurotransmitter antagonists were found to have activity against one or both of the coronaviruses (Table 1). Eleven of these were active against both, two only against SARS-CoV and three only against MERS-CoV. Two of the neurotransmitter inhibitors that inhibit both SARS-CoV and MERS-CoV are chlorpromazine hydrochloride and triflupromazine hydrochloride (Table 2). Both of these drugs inhibit the dopamine receptor and have similar chemical structures (FIG. 2A) sharing the same core structure, with the only difference being the nature of the halide group: chlorpromazine hydrochloride has a single chlorine, whilst triflupromazine hydrochloride has three fluorine surrounding a carbon. Both chlorpromazine hydrochloride and triflupromazine hydrochloride strongly inhibit SARS-CoV and MERS-CoV, with over 50% inhibition at at least one dose with micromolar IC50s (range 5.76 μM to 12.9 μM) and low toxicity (FIGS. 2B-2C). There is no significant difference between the effects of these drugs on SARS-CoV and MERS-CoV. For example triflupromazine hydrochloride inhibits both MERS-CoV and SARS-CoV with approximately the same IC50 (5.76 μM and 6.30 μM respectively, FIG. 2C). The similarity in the structure of chlorpromazine hydrochloride and triflupromazine hydrochloride would suggest that they inhibit SARS-CoV and MERS-CoV using the same mechanism of action. Chlorpromazine hydrochloride has been used to study virus entry by clathrin-mediated endocytosis of several viruses including west nile virus (WNV) and influenza virus [5-9]. SARS-CoV also utilizes the clathrin-mediated endocytosis pathway for its entry [10].

TABLE 2

Classes of compounds with activity against MERS-CoV and/or SARS-CoV in vitro.

| Compound | Commercial name | Pharmaceutical class | MERS-CoV IC50 | SARS-CoV IC50 |
|---|---|---|---|---|
| Emetine dihydrochloride hydrate | Emitine | Anti-bacterial agent | 0.014 | 0.051 |
| Chloroquine Phosphate | Chloroquine | Anti-parasitic agent | 6.275 | 6.538 |
| Hydroxychloroquine sulfate | Plaquenil | Anti-parasitic agent | 8.279 | 7.966 |
| Mefloquine | Lariam | Anti-parasitic agent | 7.416 | 15.553 |
| Amodiaquine dihydrochloride dihydrate | Camoquin, Flavoquine | Anti-parasitic agent | 6.212 | 1.274 |
| E-64-D | E-64-D | Cathepsin inhibitor | 1.275 | 0.76 |
| Gemcitabine hydrochloride | Gemzar | DNA metabolism inhibitor | 1.216 | 4.957 |
| Tamoxifen citrate | Tamoxifen, Nolvadex, Istubal, and Valodex | Estrogen receptor inhibitor | 10.117 | 92.886 |
| Toremifene citrate | Fareston, Acapodene | Estrogen receptor inhibitor | 12.915 | 11.969 |

TABLE 2-continued

Classes of compounds with activity against MERS-CoV and/or SARS-CoV in vitro.

| Compound | Commercial name | Pharmaceutical class | MERS-CoV IC50 | SARS-CoV IC50 |
|---|---|---|---|---|
| Terconazole | Terconazole | Sterol metabolism inhibitor | 12.203 | 15.327 |
| Triparanol | MER/29 | Sterol metabolism inhibitor | 5.283 | |
| Anisomycin | Flagecidin | Protein-processing inhibitor | 0.003 | 0.191 |
| Homoharringtonine | Synribo | Protein-processing inhibitor | 0.0718 | |
| Benztropine mesylate | Cogentin | Neurotransmitter inhibitor | 16.627 | 21.611 |
| Fluspirilene | Redeptin, Imap, R6218 | Neurotransmitter inhibitor | 7.477 | 5.963 |
| Thiothixene | Navane | Neurotransmitter inhibitor | 9.297 | 5.316 |
| Fluphenazine hydrochloride | Modecate | Neurotransmitter inhibitor | 5.868 | 21.431 |
| Promethazine hydrochloride | Phenergan, Promethegan, Romergan | Neurotransmitter inhibitor | 11.802 | 7.545 |
| Chlorphenoxamine hydrochloride | Phenoxene | Neurotransmitter inhibitor | 12.646 | 20.031 |
| Chlorpromazine hydrochloride | Thorazine | Neurotransmitter inhibitor | 9.514 | 12.971 |
| Thiethylperazine maleate | Torecan | Neurotransmitter inhibitor | 7.865 | |
| Triflupromazine hydrochloride | Vesprin | Neurotransmitter inhibitor | 5.758 | 6.398 |
| Clomipramine hydrochloride | Anafranil | Neurotransmitter inhibitor | 9.332 | 13.238 |
| Imatinib mesylate | Gleevac | Kinase signaling inhibitor | 17.689 | 9.823 |
| Nilotinib | Tasigna | Kinase signaling inhibitor | 5.468 | 2.1 |

Figure 3A:
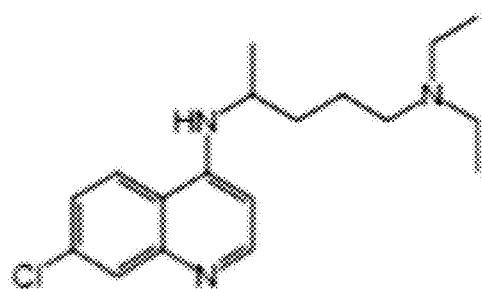
FIGS. 3A-3C show inhibition of MERS-CoV and SARS-CoV with Chloroquine.
Figure 3B:
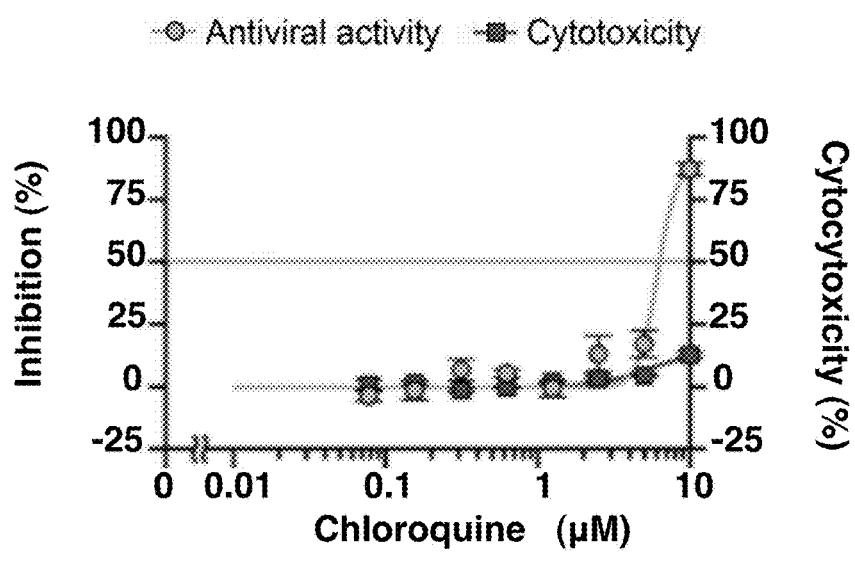
Figure 3C:
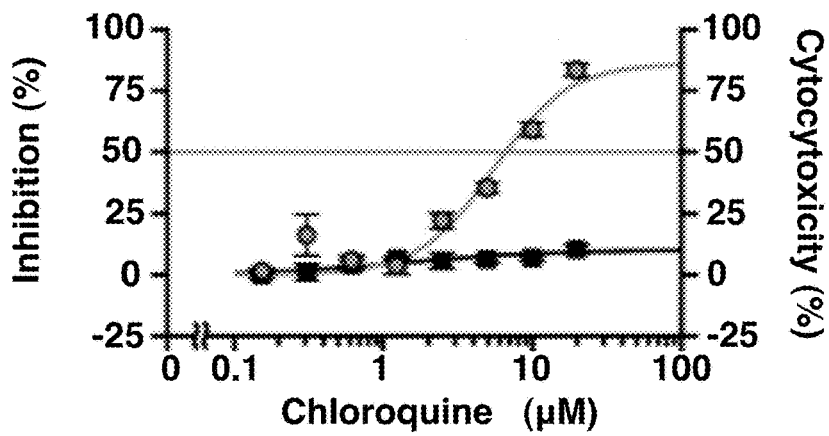
Figure 4A:
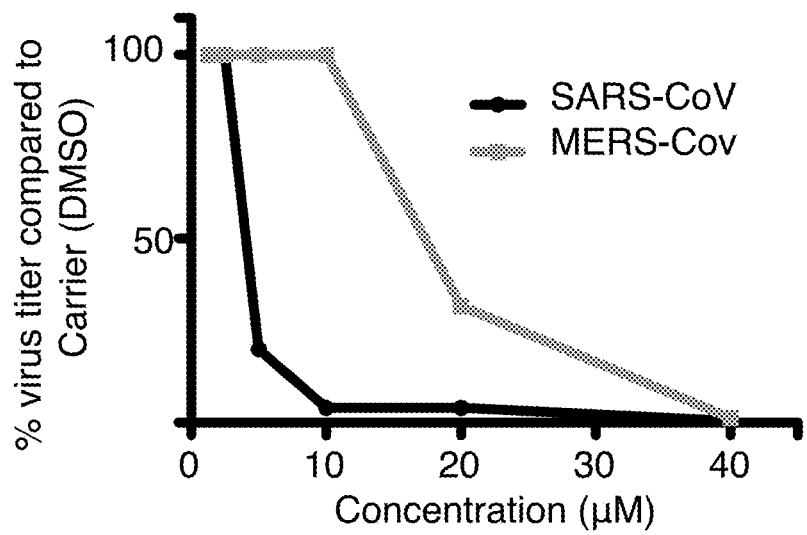
FIGS. 4A-4B show in vitro inhibition of MERS-CoV and SARS-CoV virus growth by Chlorpromazine (FIG. 4A) and Chloroquine (FIG. 4B). Vero E6 cells were pretreated with Chlorpromazine, Chloroquine or 0.05% DMSO vehicle for 2 hours before infection with each virus at an MOI of 3. At 24 hours post infection for SARS-CoV and 48 hours post infection for MERS-CoV (Jordan), supernatant was collected and analyzed by TCID50 assay. Graphed is the percent of virus produced at each concentration compared to DMSO alone.
Figure 4B:
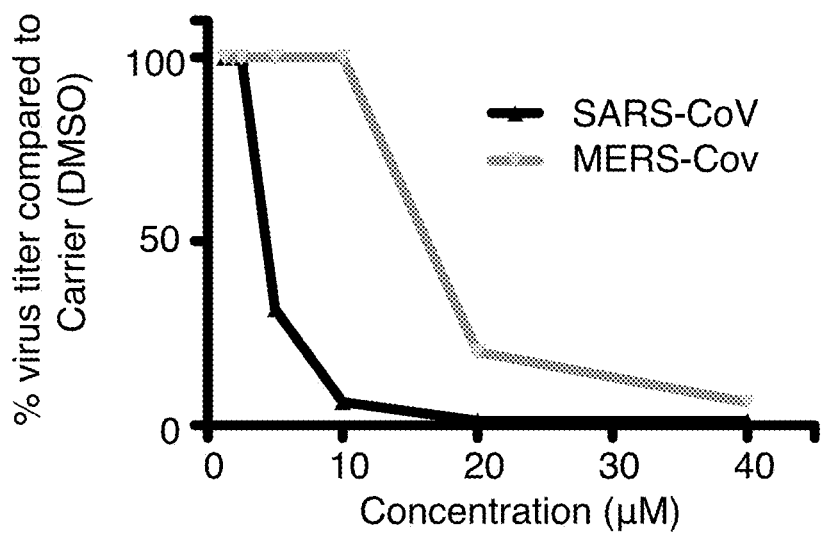

Chloroquine is a well known anti-parasitic drug that is a weak base which increases the pH of acidic vesicles. It is effective against hCoV-OC43 in culture as well as several other viruses including HIV(31). Chloroquine inhibits MERS-CoV and SARS-CoV with an EC50 of 9.51 uM and 12.97 uM concentration, respectively (FIGS. 3A-3B). To identify whether the drugs blocked virus production, a virus inhibition assay was performed in Vero E6 (African green monkey kidney cells) (FIGS. 4A-4B) and MRC5 (human lung fibroblasts) with SARS-CoV and MERS-CoV. Cells were pretreated for 2 hours before infection with a range of 1.25 mM to 40 mM of each drug, then infected with an MOI of 3 in each well. Both viruses are inhibited by both drugs with SARS-CoV being more sensitive. For SARS-CoV, the EC50 to Chlorpromazine is 4.86 mM and to Chloroquine is 6.43 mM. For MERS-CoV, the EC50 for Chlorpromazine is 19.4 mM and for Chloroquine is 18.42 mM. MRC5 EC50 and curves are similar to Vero E6 cell numbers.

Figure 5A:
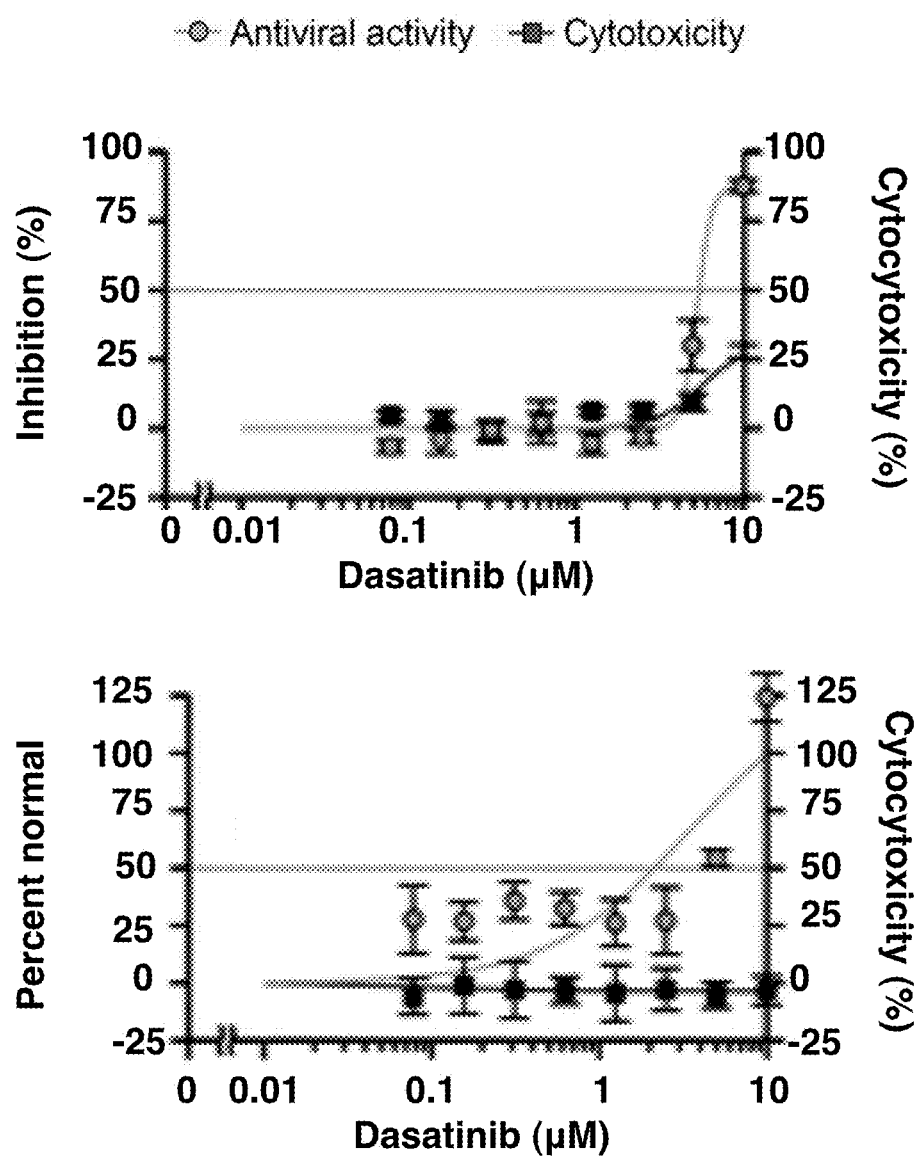
FIGS. 5A-5B show antiviral activity of dastinib and imatinib mesylate. Vero E6 cells were infected with MERs-CoV (top) or SARS-CoV (bottom) at an m.o.i. of 0.1 and treated for 48 h with eight doses of dastinib (FIG. 5A) or imatinib mesylate (FIG. 5B). Antiviral activity is shown in with open circle and cytotoxity is shown with shaded circle. IC50 values are indicated. Results are representative of one experiment (mean±SEM; n=2).
Figure 5B:
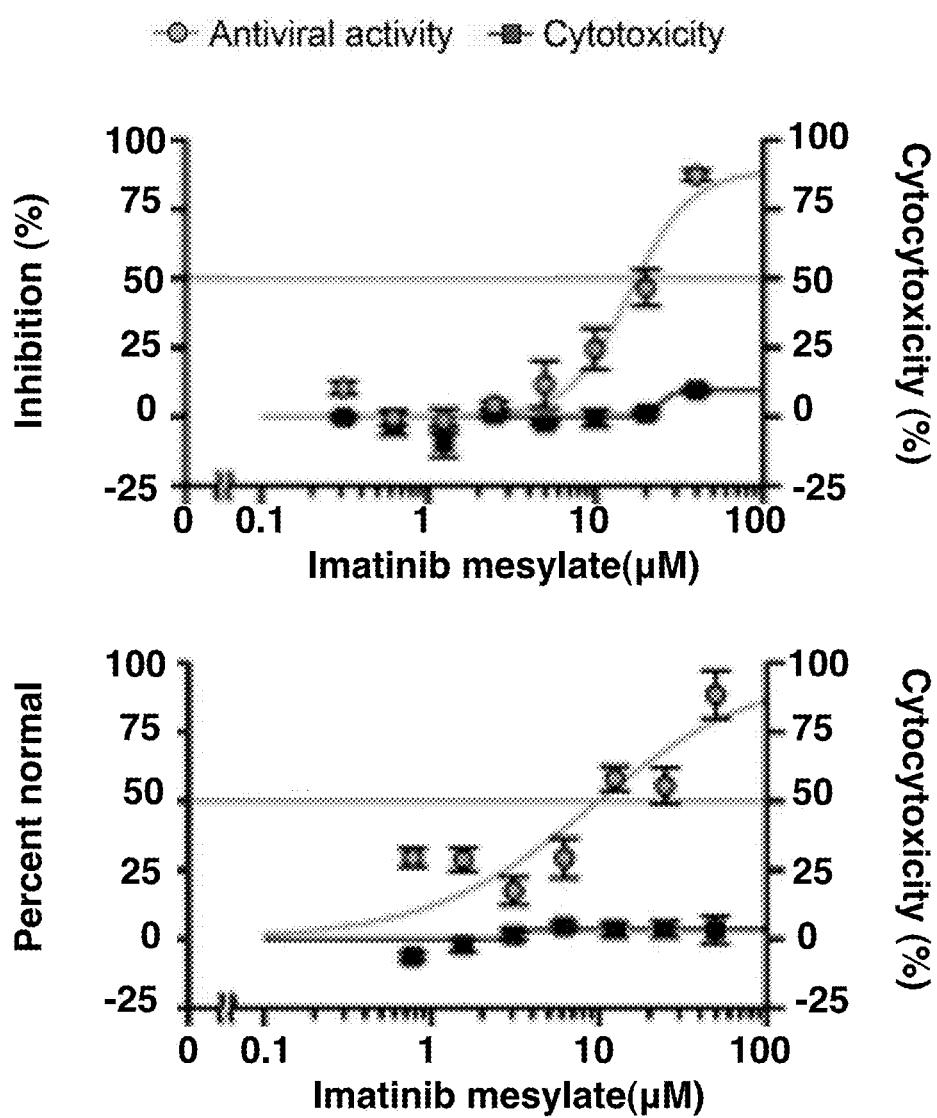

Three inhibitors of the kinase signaling pathway were identified, two (imatinib mesylate and dasatinib) that are active against both MERS-CoV and SARS-CoV, and one (nilotinib) that inhibits SARS-CoV only. Imatinib mesylate and dasatinib are known inhibitors of the Abelson murine leukemia viral oncogene homolog 1 (ABL1) pathway. The ABL1 pathway is a signaling pathway involved in cell differentiation, cell adhesion, and the cellular stress response. Overactivation of the ABL1 pathway can lead to chronic myelogenous leukemia. Both imatinib mesylate and dasatinib were developed and approved as inhibitors of this pathway for treating human cancers, including chronic myelogenous leukemia (33, 34). Both imatinib mesylate and dasatinib inhibit SARS-CoV and MERS-CoV with micromolar EC50s (range, 2.1 to 17.6 µM) and low toxicity (FIGS. 5A and 5B). SARS-CoV does appear to be more sensitive to both ABL1 inhibitors. For example, the EC50 of dasatinib against SARS-CoV is 2.1 µM, whereas for MERS-CoV the EC50 is 5.4 µM (FIG. 5A). A third ABL1 inhibitor, nilotinib, was also used. Nilotinib inhibited SARS-CoV with a micromolar EC50 and low toxicity but does not significantly inhibit MERS-CoV, with the maximum inhibition of MERS-CoV being 39% at the highest dose tested. However, the fact that nilotinib is able to inhibit SARS-CoV and partially inhibit MERS-CoV further points to the importance of the ABL1 pathway in coronavirus replication. Imatinib mesylate has been shown to block egress of Ebola virus and of poxviruses and entry of coxsackievirus (20, 35, 36).

Figure 6A:
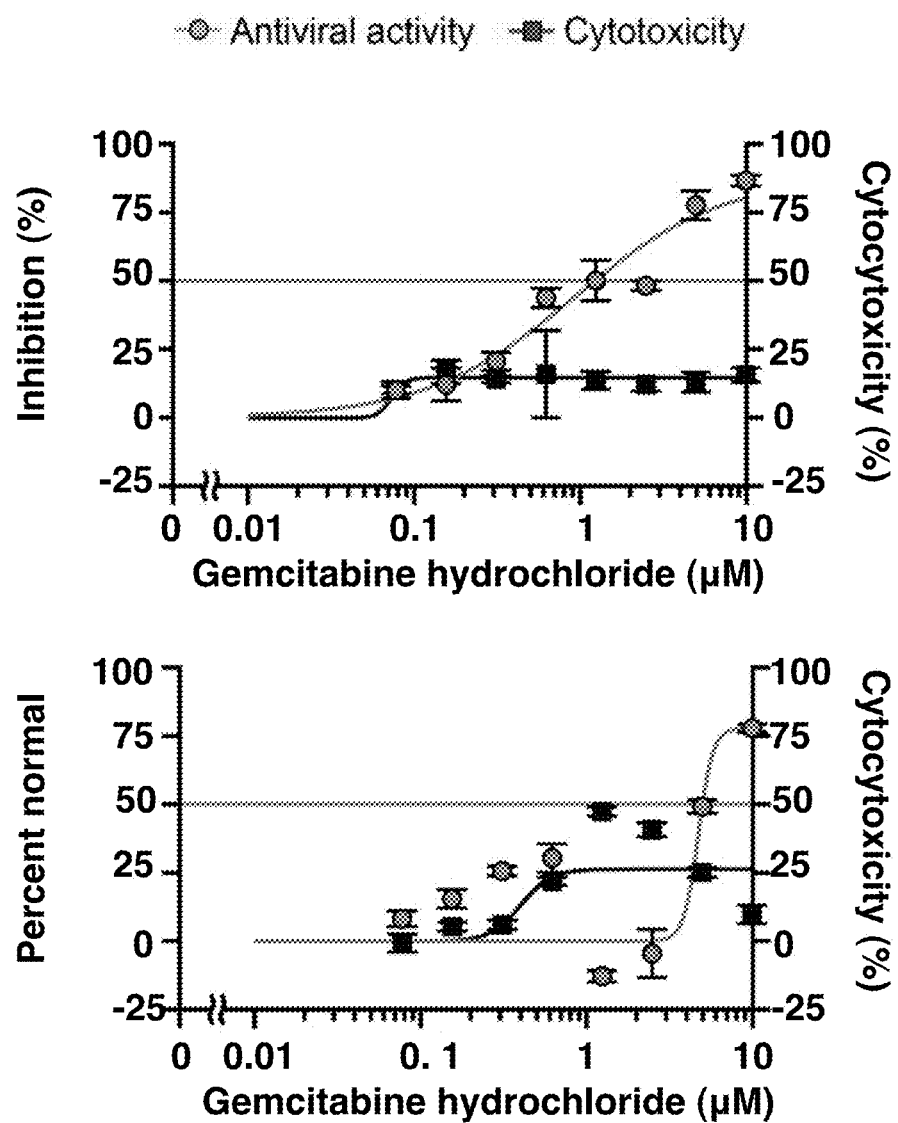
FIGS. 6A-6B show antiviral activity of gemcitabine hydrochloride and toremifene citrate. Vero E6 cells were infected with MERs-CoV (top) or SARS-CoV (bottom) at an m.o.i. of 0.1 and treated for 48 hours with eight doses of gemcitabine hydrochloride (FIG. 6A) or toremifene citrate (FIG. 6B). Antiviral activity is shown with light circles and cytotoxity is shown with dark squares. IC50 values are indicated. Results are representative of one experiment (mean±SEM; n=2).

Gemcitabine hydrochloride is a deoxycytidine analog that inhibits DNA synthesis and repair. Gemcitabine hydrochloride inhibits both MERS-CoV and SARS-CoV with micromolar EC50s (1.2 µM and 4.9 µM, respectively) and low toxicity (FIG. 6A). Four DNA synthesis inhibitors were active against at least one coronavirus (Table 1). These data also demonstrate the importance of screening large drug sets, rather than targeted screens of suspected inhibitors, as it may not have been immediately obvious that a DNA synthesis inhibitor would have any effect on the replication of an RNA virus.

Figure 6B:
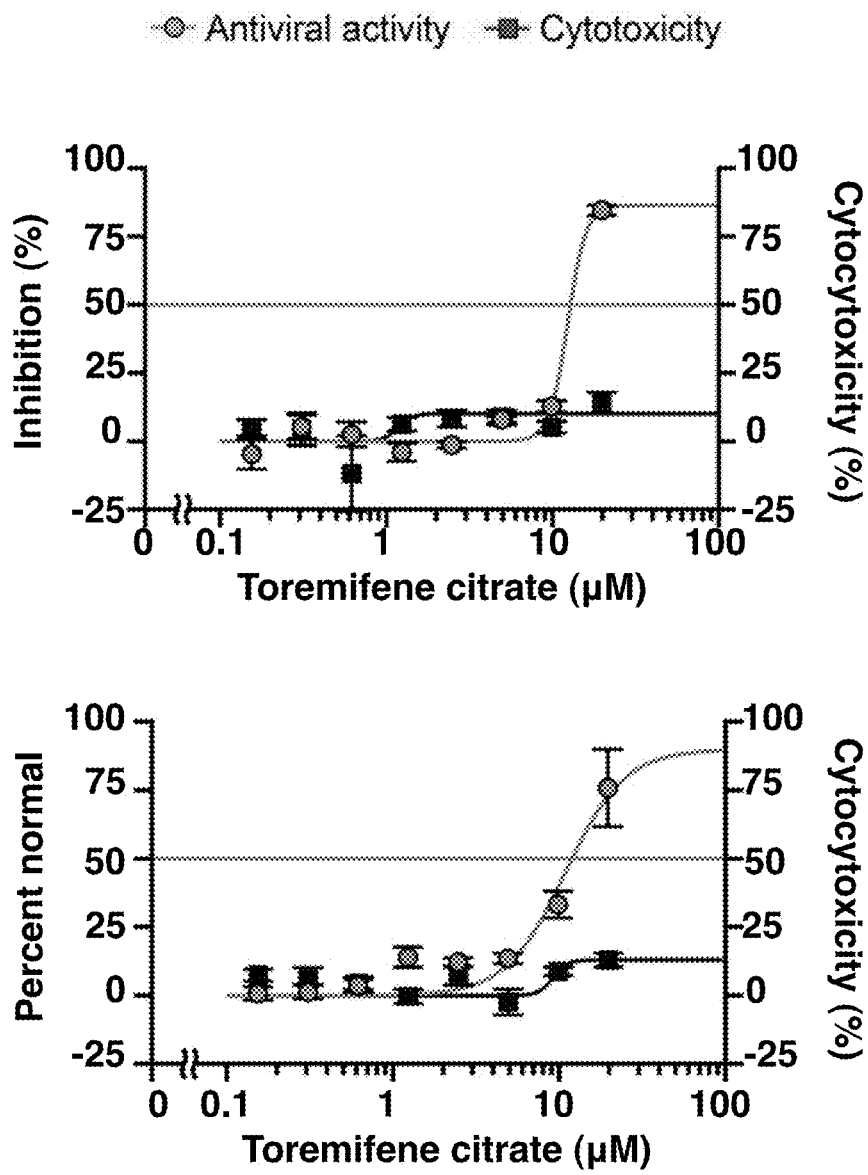

Toremifene citrate is an estrogen receptor 1 antagonist that inhibits both MERS-CoV and SARS-CoV with micromolar EC50s (12.9 µM and 11.97 µM, respectively) and low toxicity (FIG. 6B). Toremifene citrate has been tested against several filoviruses and was shown to block filovirus entry (21, 37). In the screens described here, there were five estrogen receptor inhibitors that blocked at least one coronavirus (Table 1), and two of these blocked both MERS-CoV and SARS-CoV with micromolar EC50s (Table 2) and low toxicity. While the antiviral mechanism against MERS-CoV and SARS-CoV is unknown, these results suggest that estrogen receptor 1 inhibitors have the potential for broad-spectrum antiviral activity.

Figure 7A:
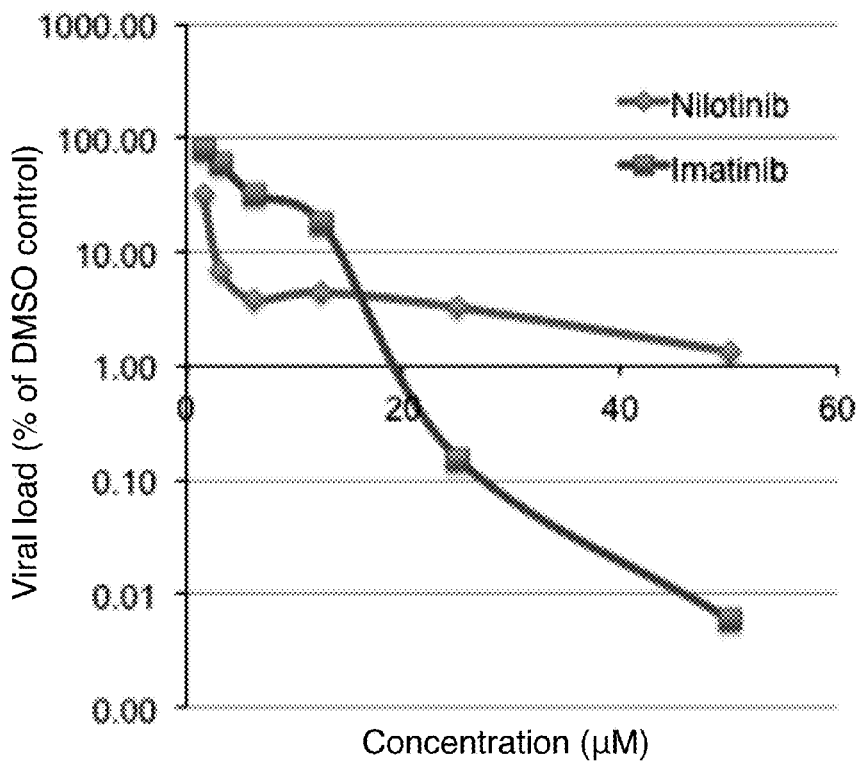
FIGS. 7A-7B show inhibition of MERS-CoV and SARS-CoV replication in vitro. Vero cells were pretreated with either Imatinib or Nilotinib at the shown concentrations. After 2 hours, cells were infected with MERS-CoV (FIG. 7A) or SARS-CoV (FIG. 7B) at an MOI of 1. At 24 hours (for SARS-CoV) or 48 hours (for MERS-CoV) post infection, media was analyzed by TCID50 to assess viral release. The TCID50 amount was compared to a control and graphed above as % of control.
Figure 7B:
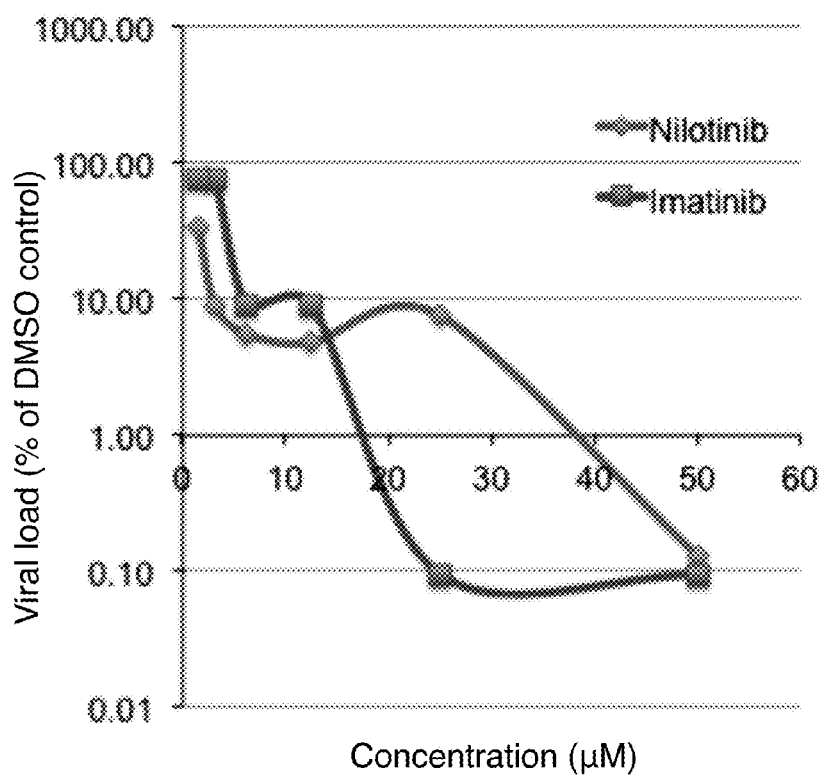

Imatinib and Nilotinib were both found to also have an effect on virus replication. Vero E6 cells were treated with a concentration curve of Imatinib or the related ABL kinase inhibitor Nilotinib for 2 hours before infection with each virus at an moi of 1. At 24 hours for SARS-CoV and 48 hours for MERS-CoV, media was collected and analyzed by a TCID50 assay (FIGS. 7A-7B). IC50 values were calculated for each drug and virus. Imatinib has an IC50 value for SARS-CoV at 6.65 uM and MERS-CoV at 14.5 uM. Nilotinib has an IC50 value for SARS-CoV of 2.3 uM and MERS-CoV of 9.53 uM.

Figure 8A:
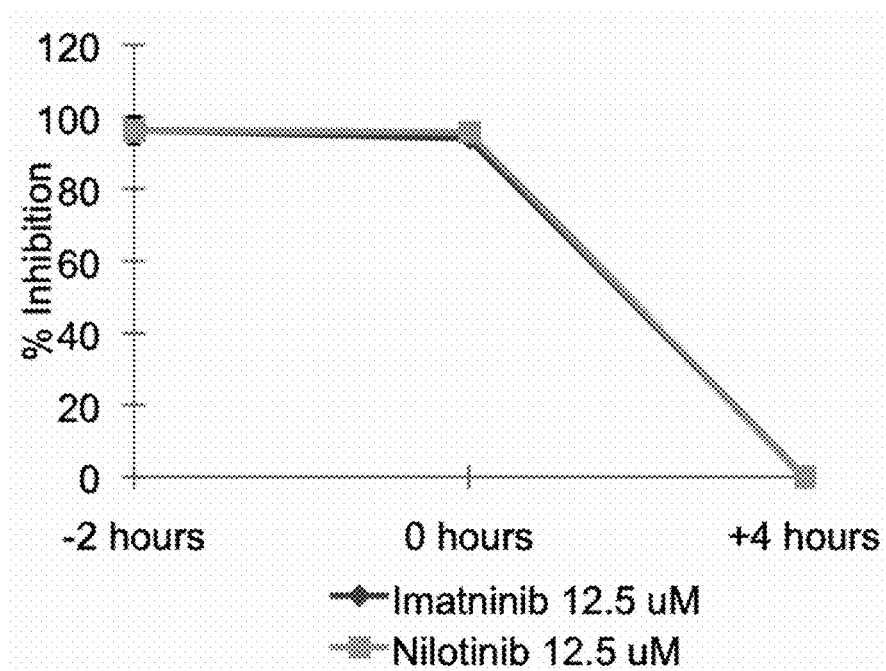
FIGS. 8A-8B show time of addition experiments with Imatinib and Nilotinib. Vero E6 cells were either pretreated for 2 hours, not pre-treated or treated at 4 hours post infection with either MERS-CoV (FIG. 8A) and SARS-CoV (FIG. 8B). Supernatant was collected at 24 and 48 hours post infection and analyzed the amount of virus produced into the media by TCID50 assay. There is little effect when given after entry of the virion, however virus is significantly inhibited by both drugs when given before or at the time of infection.
Figure 8B:
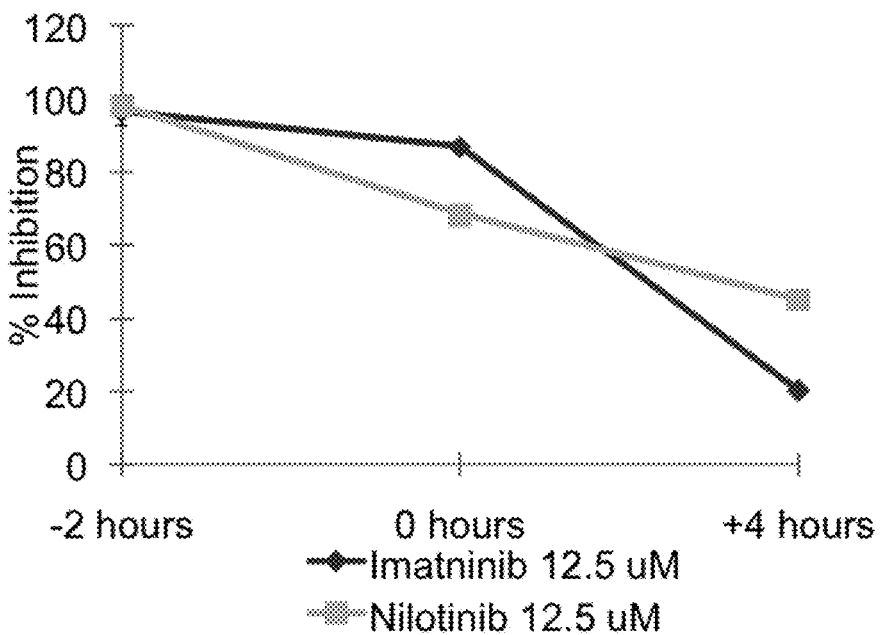

From the Imatinib and Nilotinib time of addition studies, it was found that when drugs are added before infection, there is significant inhibition of virus growth. When the drug is added at the time of infection, there is inhibition of virus growth (FIGS. 8A-8B). However, when drugs are added 4 hours post infection, there is little inhibition of either virus.

This demonstrates that the ABL kinase inhibitors are acting early in the viral life cycle, potentially at either virus entry, endosomal trafficking, fusion with endosomal membrane or at the level of transcription of viral RNA.

Figure 9A:
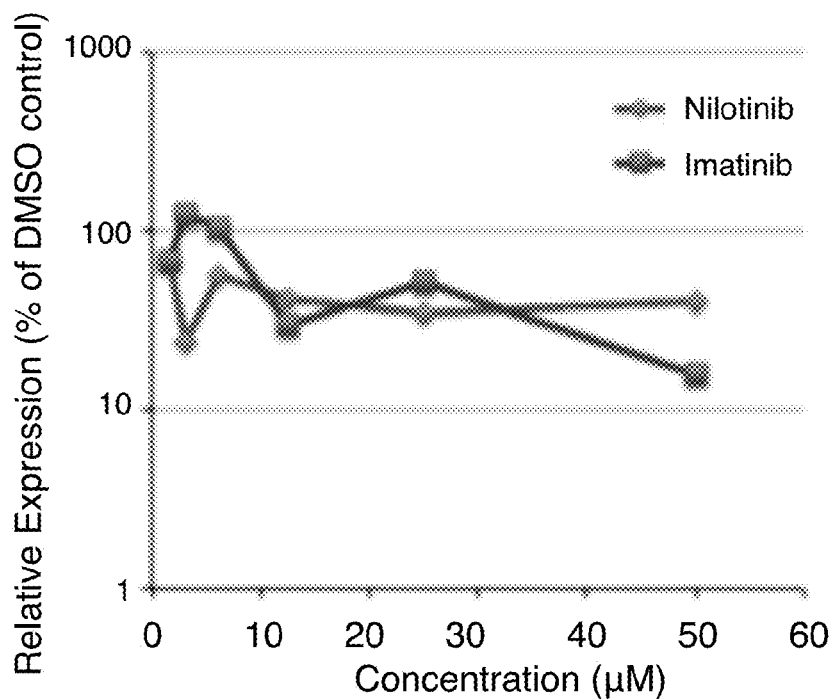
FIGS. 9A-9B show that Imatinib and Nilotinib inhibit MERS-CoV viral RNA production. Imatinib and Nilotinib where added across a concentration range at either 2 hours before infection (FIG. 9A) or 4 hours after infection (FIG. 9B). Viral RNA was analyzed by Realtime PCR for the production of leader containing RNA. The results are plotted on a log scale as relative expression compared to DMSO control. Both drugs inhibited MERS-CoV viral RNA production when added before infection however failed when added 4 hours post infection.
Figure 9B:
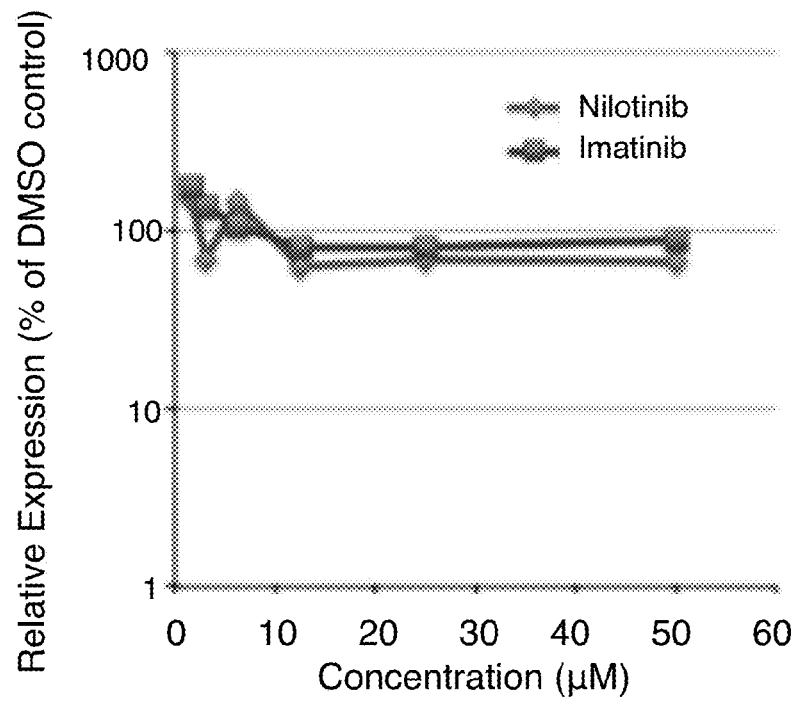

Coronaviruses add a specific leader to newly transcribed viral RNA which can be detected by using specific primers to the leader sequence and analyzing by Realtime PCR. When cells are pretreated for 2 hours before infection with a concentration range of Imatinib and Nilotinib, there is a reduction in the production of leader containing viral RNA for MERS-CoV (FIGS. 9A-9B). When each drug is added 4 hours after infection there is no reduction of viral leader containing RNA. This finding correlates with the time of addition experiments assaying for virus production. This data suggests that Imatinib and Nilotinib are either inhibiting a step from entry of the viruses through the production of viral RNA.

The viral pseudotype assay was used to identify where Imatinib acts in the entry steps of the SARS-CoV and MERS-CoV. Using HIV/SARS-S and HIV/MERS-S demonstrated that without drug, there are high levels of BlaM entry into the cytoplasm as evidenced by cleavage of CCF2 and fluorescence. Using this assay cells were pre-treated with Imatinib and Gemcitabine before infecting with MERS-S pseudoparticles. CCF2 cleavage readout showed that with HIV/MERS-S and no drug, only DMSO carrier, there is a high level of fluorescence (this is set at 100%, raw value is ~60% entry efficiency). When cells were pretreated with Imatinib, there was very little CCF2 signal (7.8% of control). However with Gemcitabine, which works late in infection, not early, there is little inhibition compared to control (95% of control). By analyzing viral RNA transcription, Imatinib blocks a step before transcription of the viral genes. Imatinib blocks either viral envelope fusion with the endosomal membrane or a step before that such as Spike cleavage, endosomal protein trafficking/maturation or entry of virions into endosomes.

Figure 10:
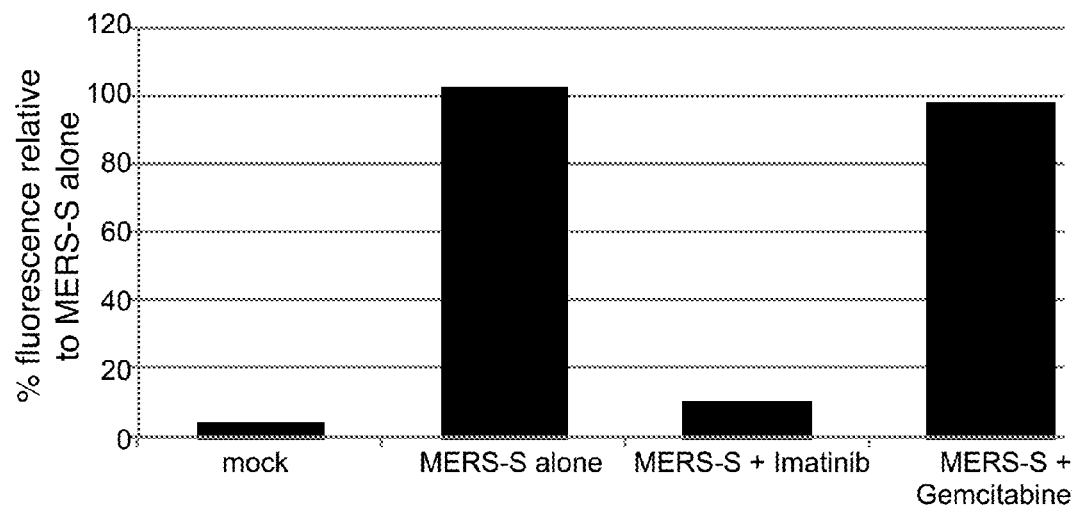
FIG. 10 shows Imatinib blocks endosomal fusion in HIV/MERS-S Pseudotype assay. Vero cells were treated with Imatinib (12.5 uM), Gemcitabine (25 uM) 2 hours post infection with MERS-S pseudoparticles. Graphed is % fluorescence of assay by FACS, relative to MERS-S pseudotype alone (second from left).
Figure 11:
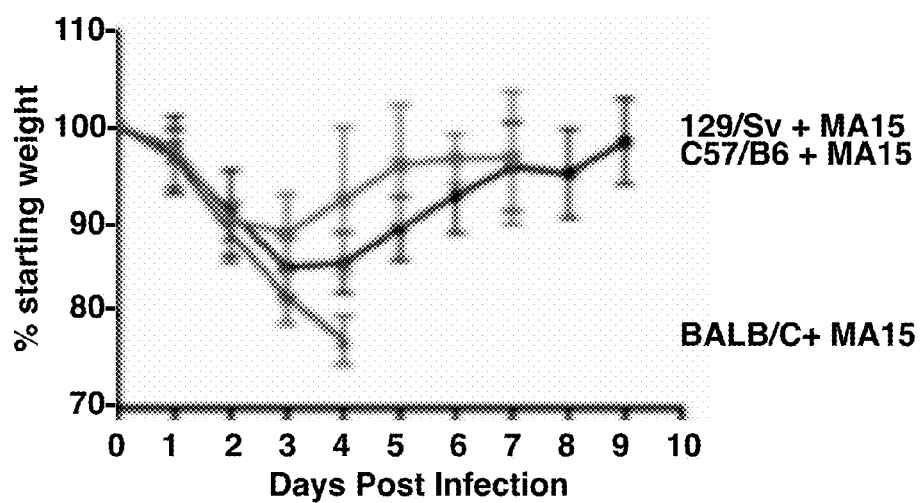
FIG. 11 shows weight loss of MA15 SARS-CoV mouse model in BALB/c, 120/Sv and C57B/6 mice.

The viral pseudotype assay identified where Imatinib acts in the entry steps of the SARS-CoV and MERS-CoV. The HIV/SARS-S and HIV/MERS-S demonstrated that without drug, there are high levels of BlaM entry into the cytoplasm as evidenced by cleavage of CCF2 and fluorescence (FIG. 10).

Drugs in Mouse Model

Figure 12A:
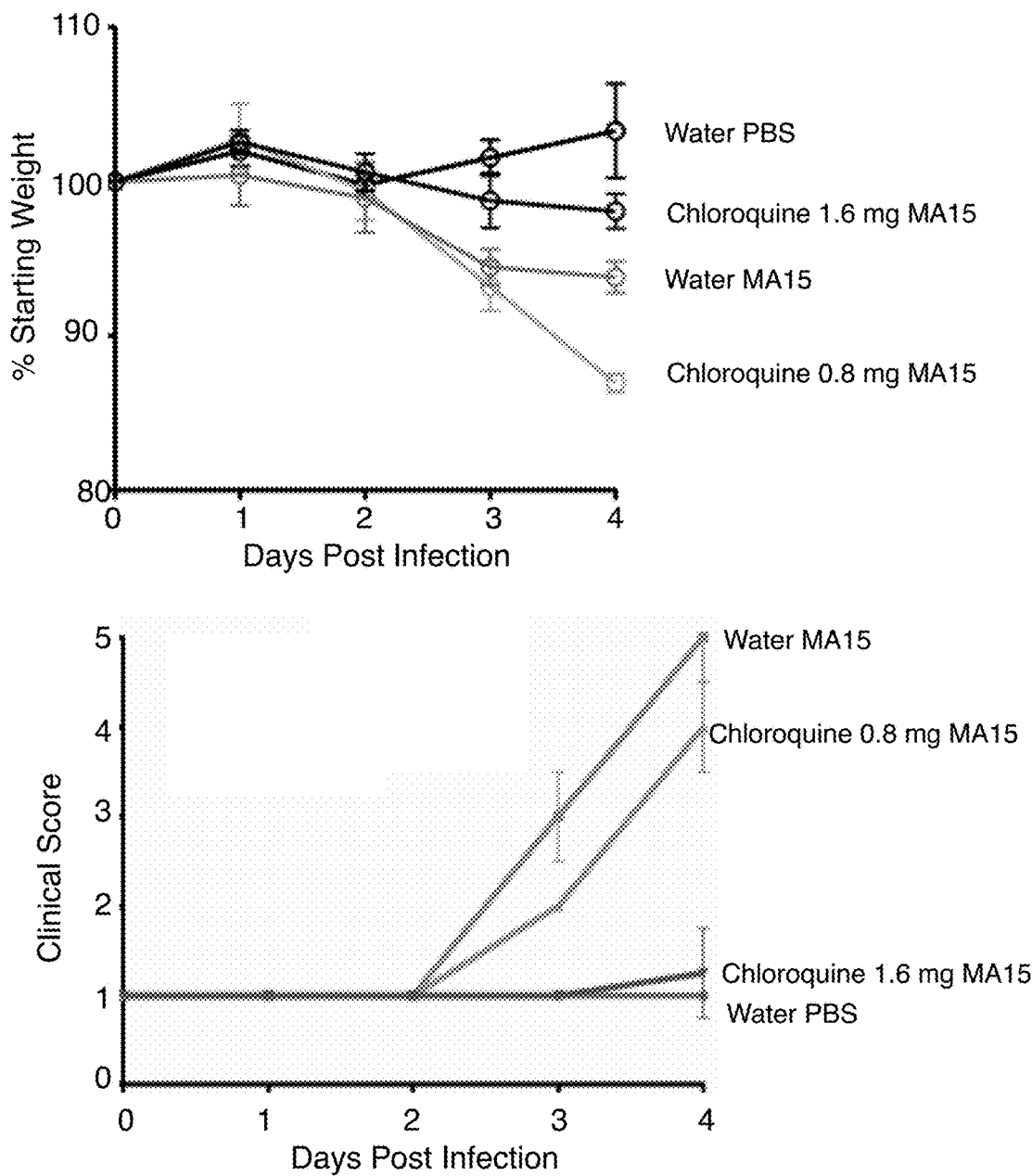
FIGS. 12A-12B show chloroquine (FIG. 12A) and chlorpromazine (FIG. 12B) protect MA15 infected BALB/c mice from weight loss (left panels) and clinical disease (right panels). A dose of 1.6 mg/mouse of chloroquine and 100 µg/mouse of chlorpromazine blocks all weight loss seen in MA15 infection of BALB/c and reverses clinical score to mock infected levels.
Figure 12B:
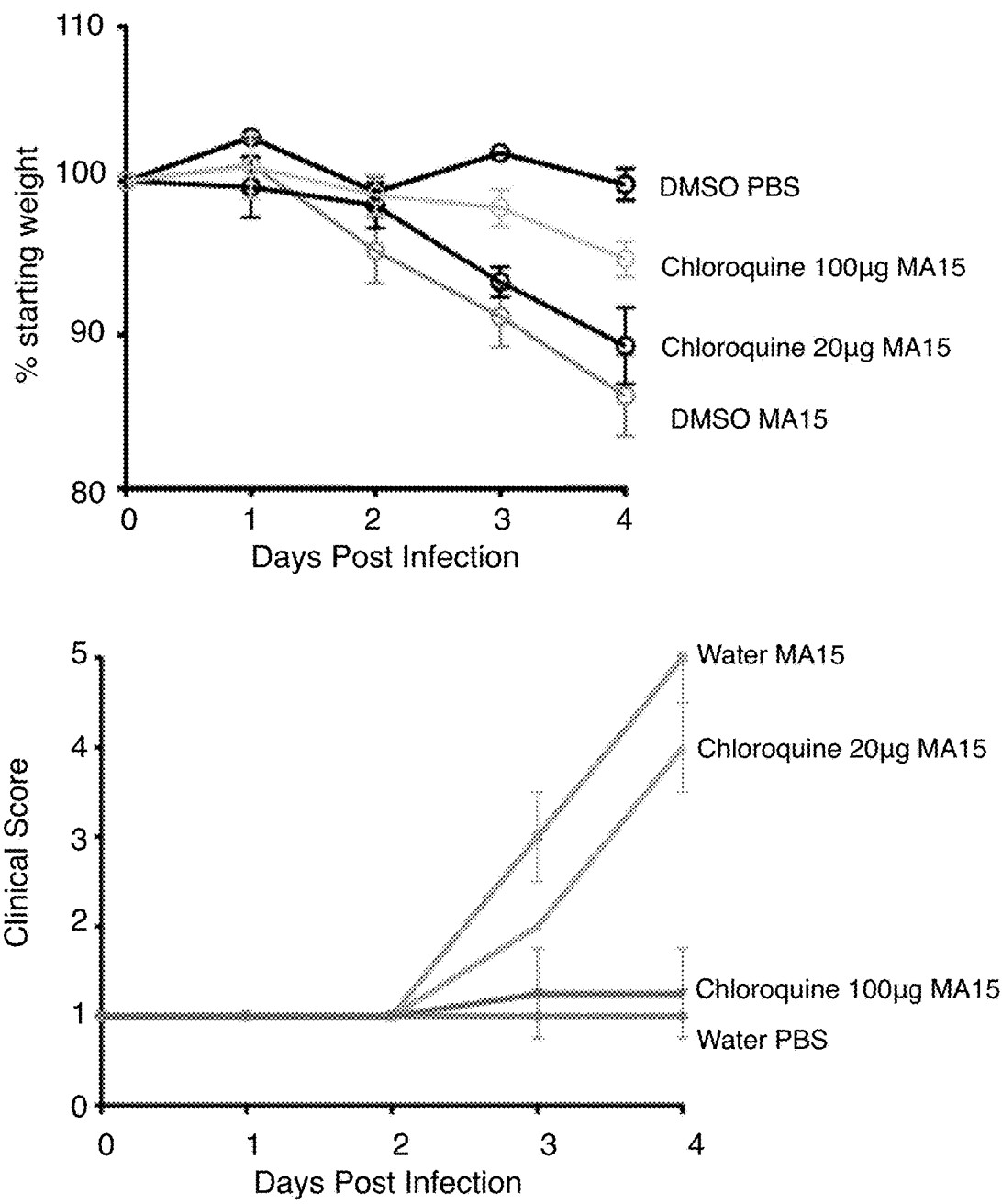

In the experiments, control injected mice lose 15-20% of their body weight through 4 days post infection with MA15 challenge. Their clinical score of morbidity rises from 1 at day 0 to a 5 at day 4, displaying severely ruffled fur, labored breathing and minimal movement in the cage. For the drug treated groups, there was a reversal of weight loss and clinical score for Chlorpromazine and Chloroquine treated mice (FIGS. 12A-12B).

In the groups treated with 1.6 mg/mouse dose of Chloroquine or the 100 mg/mouse dose of Chlorpromazine, mice lose less than 5% of their starting weight throughout the 4 days and have a near complete protection from clinical disease. There was no distinguishable difference between the clinical score of PBS mice and the mice in the higher dosed drug groups. Both lower dosed drug groups, 0.8 mg/mouse of Chloroquine and 20 mg/mouse of Chlorpromazine had moderate alterations in weight loss however displayed clinical symptoms that were statistically lower than water treated mice but still looked clinically sick. Virus titer was not reduced in even the higher drug treated groups.

Discussion

Screening of a library of 290 drugs either clinically developed or with a well-defined cellular pathway identified 27 compounds with activity against MERS-CoV and SARS-CoV, 33 compounds with activity against MERS-CoV alone, and 6 compounds with activity against SARS-CoV alone.

The drugs identified here belong to 13 different classes of pharmaceutical drugs. For two of the classes, kinase signaling inhibitors and estrogen receptor antagonists, previous work with other viruses has given insight into how these drugs may affect viral infections. Three tyrosine kinase inhibitors, imatinib mesylate (Gleevec), nilotinib (Tasigna), and dasatinib, were developed to treat human cancers and were later shown to have activity against several viruses, including poxviruses and Ebola virus (20, 36). Mechanism of action studies revealed that Abl1 tyrosine kinase regulates budding or release of poxviruses and Ebola virus. Kinase signaling may also be important for replication of two members of the Coronaviridae family. Imatinib mesylate and dasatinib inhibit MERS-CoV and SARS-CoV, while nilotinib inhibits only SARS-CoV. In vivo studies performed in the mouse model of vaccinia virus infection showed that imatinib mesylate was more effective than dasatinib in blocking dissemination of the virus, and this was attributed to the immunosuppressive effect of dasatinib (36). Nevertheless, dasatinib may have value for treating coronaviral infections if a dosing regimen that minimizes immunotoxicity while still blocking viral replication can be defined. Imatinib mesylate (Gleevec) and nilotinib (Tasigna) are FDA-approved oral cancer medicines (38).

Estrogen receptor modulators represent another class of FDA-approved drugs that have potential as antivirals in the clinic. Toremifene citrate, which blocks both MERS-CoV and SARS-CoV, has been shown to inhibit filoviruses (21). Mechanism of action studies showed that the drug acts at a late step of virus entry and may inhibit trafficking of the virus to the late endosome or triggering of fusion for filoviruses (21, 37). Interestingly, the estrogen signaling pathway is not involved in the virus entry step, indicating that these drugs may have off-target effects or the estrogen signaling pathway plays an as-yet-undiscovered role in filovirus biology. Toremifene citrate also showed activity in the mouse model of Ebola virus infection (21).

The screen also identified antiviral actives in the pharmaceutical class of neurotransmitter receptor antagonists. These antagonists have been developed for psychiatric care as antipsychotics, antiemetics, anticholinergics, and antidepressants and predominantly act by blocking the dopamine receptor or H1 receptor (antihistamine). Chlorpromazine was shown to inhibit clathrin-mediated endocytosis of several viruses by preventing the formation of clathrin-coated pits at the plasma membrane (27). This drug is currently approved by the FDA as an antipsychotic and for the treatment of nausea (39) and is occasionally used for short-term use as off-label treatment of severe migraine (40), making it a promising candidate for testing as a broad-spectrum antiviral. Astemizole is a strong antagonist of the H1 receptor and is an inhibitor of malaria in two animal models of malaria with a mechanism of action similar to that of chloroquine (41). Although astemizole was withdrawn from the U.S. market in 1999, it may be worthwhile to reexamine this drug or existing analogs for short-term use in an acute infection. Previous work on chloroquine in coronavirus infections by Barnard et al. has found that while the drug inhibits viral replication in vitro, chloroquine did not show efficacy in reducing SARS-CoV virus titers in a nonlethal mouse model (42).

The screen identified 33 MERS-CoV actives (Table 1), and the two largest classes were cytoskeleton inhibitors (8 drugs) and ion channel inhibitors (11 drugs). Drugs targeting the cytoskeleton specifically interfere with microtubule polymerization and are antimitotics developed for treatment of cancer. Some of them, such as nocodazole, have also been used in cell biology labs to synchronize the cell division cycle. Nocodazole's ability to depolymerize microtubules has been used to investigate the entry pathway of West Nile Virus (WNV), and results show that an intact microtubule network is necessary for trafficking of internalized WNV from early to late endosomes (27). This drug had high activity against MERS-CoV but had no activity against SARS-CoV, suggesting that, in addition to the application as therapeutics, these drugs may also have value in further elucidating differences in the virus replication cycle of MERS-CoV and SARS-CoV.

Two of the 9 ion channel inhibitors, monensin and salinomycin sodium, with activity against MERS-CoV, represent polyether ionophores that are well-recognized candidates for anticancer drugs (43, 44). Studies on the mechanism of anticancer activity have shown that these compounds affect cancer cells by increasing their sensitivity to chemotherapy and reversing multidrug resistance (monensin) in human carcinoma. Furthermore, ionophore antibiotics also inhibit chemoresistant cancer cells by increasing apoptosis, and salinomycin was specifically shown to be able to kill human cancer stem cells (45). Interestingly, these compounds affected MERS-CoV but not SARS-CoV, indicating that MERS-CoV is uniquely susceptible to ionophore activities. Monensin has also been reported to inhibit La Crosse virus and Uukuniemi virus infection by blocking the formation and egress of virus particles (46, 47).

Overall, several pharmaceutical classes of drugs were identified that could be beneficial for treatment of coronaviral infections. Chlorpromazine hydrochloride and chloroquine diphosphate were also identified in a similar but independent study described by A. H. de Wilde et al. (48). These drugs appear to target host factors rather than viral proteins specifically, and treatment of viral infections in patients aimed at host factors could reconfigure overt manifestations of viral pathogenesis into a less virulent subclinical infection and lower adverse disease outcome (38).

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

The following references are cited herein:
1. WHO. 2003. Summary of probable SARS cases with onset of illness from 1 Nov. 2002 to 31 Jul. 2003. www.who.int/csr/sars/country/table2004_04_21/en/index.html.
2. Zaki et al., 2012. N. Engl. J. Med. 367:1814-1820.
3. The WHO MERS-Cov Research Group. 12 Nov. 2013. State of knowledge and data gaps of Middle East respiratory syndrome coronavirus (MERS-CoV) in humans. PLoS Curr. 5:pii:ecurrents.outbreaks.
0bf719e352e7478f7478ad7485fa30127ddb30128.
4. Lu et al., 2013. Nature 500:227-231.
5. Raj et al., 2013. Nature 495:251-254.
6. Alagaili et al., 2014. mBio 5:e00884-14.
7. Annan et al., 2013. Emerg. Infect. Dis. 19:456-459.
8. Ithete et al., 2013. Emerg. Infect. Dis. 19:1697-1699.
9. Memish et al., 2013. Emerg. Infect. Dis. 19:1819-1823.
10. Meyer et al., 2014. Emerg. Infect. Dis. 20:552-559.
11. Perera et al., 2013. Euro Surveill. www.eurosurveillance.org/ViewArticle.aspx?ArticleId=20574.
12. Reusken et al., 2013. Lancet Infect. Dis. 13:859-866.
13. Zhao et al., 2014. Proc. Natl. Acad. Sci. U.S.A 111:4970-4975.
14. Brown et al., 2013 Jul. 29. saric.tghn.org/site_media/media/articles/Decision_Support_Document_v1_1_20130729.pdf
15. Falzarano et al., 2013. Sci. Rep. 3:1686.
16. Falzarano et al., 2013. Nat. Med. 19:1313-1317.
17. Al-Tawfiq et al., 2014. Int. J. Infect. Dis. pii:S1201-9712(13)00376-7.
18. Chan et al., 2013. J. Infect. 67:606-616.
19. Hart et al., 9 Dec. 2013. J. Gen. Virol.
20. Garcia et al., 2012. Sci. Transl. Med. 4:123ra24.
21. Johansen et al., 2013. Sci. Transl. Med. 5:190ra179.
22. Madrid et al., 2013. PLoS One 8:e60579.
23. de Groot et al., 2013. J. Virol. 87:7790-7792.
24. Roberts et al., 2007. PLoS Pathog. 3:e5.
25. Lehar et al., 2009. Nat. Biotechnol. 27:659-666.
26. Bosch et al., 2008. J. Virol. 82:8887-8890.
27. Chu J J, Ng M L. 2004. J. Virol. 78:10543-10555.
28. Joki-Korpela et al., 2001. J. Virol. 75:1958-1967.
29. Krizanova et al., 1982. Acta Virol. 26:209-216.
30. Nawa et al., 2003. J. Gen. Virol. 84:1737-1741.
31. Pho et al., 2000. J. Virol. 74:2288-2292.
32. Inoue et al., 2007. J. Virol. 81:8722-8729.
33. Tolomeo et al., 2009. Anticancer Agents Med. Chem. 9:853-863.
34. Wolf D, Rumpold H. 2009. Drug Saf. 32:1001-1015.
35. Coyne C B, Bergelson J M. 2006. Cell 124:119-131.
36. Reeves et al., 2011. J. Virol. 85:21-31.
37. Shoemaker et al., 2013. PLoS One 8:e56265.
38. McFadden G. 2005. Nat. Med. 11:711-712.
39. American Society of Health-System Pharmacists. 2014. Chlorpromazine. Chlorpromazine hydrochloride. In McEvoy G K (ed), AHFS drug information. American Society of Health-System Pharmacists, Bethesda, Md.
40. Logan P, Lewis D. 2007. Emerg. Med. J. 24:297-300.
41. Chong et al., 2006. Nat. Chem. Biol. 2:415-416.
42. Barnard et al., 2006. Antivir. Chem. Chemother. 17:275-284.
43. Gupta et al., 2009. Cell 138:645-659.
44. Huczynski A. 2012. Bioorg. Med. Chem. Lett. 22:7002-7010.
45. Koo et al., 2013. Cell Death Dis. 4:e693.
46. Cash P. 1982. J. Gen. Virol. 59:193-196.
47. Kuismanen et al., 1985. J. Virol. 55:813-822.
48. de Wilde et al., 2014. Antimicrob. Agents Chemother. 58:4875-4884.

What is claimed is:
1. A method for treating a coronavirus infection in a subject, comprising the step of:
   administering to said subject a therapeutically effective amount of a kinase signaling inhibitor selected from the group consisting of imatinib mesylate, nilotinib hydrochloride and dasatinib.
2. The method of claim 1, wherein said coronavirus is Middle East respiratory syndrome coronavirus or severe acute respiratory syndrome coronavirus.
3. The method of claim 1, wherein said kinase signaling inhibitor inhibits viral activity by at least 50%.

4. The method of claim 1, wherein said kinase signaling inhibitor inhibits viral RNA production and/or blocks endosomal fusion.

5. The method of claim 1, wherein said kinase signaling inhibitor is administered in a concentration range of about 50 mg/kg to about 500 mg/kg per day.

6. The method of claim 1, further comprising:
administering an antiviral drug.

7. The method of claim 6, wherein said antiviral drug is selected from the group consisting of an interferon, ribavirin, adefovir, tenofovir, acyclovir, brivudin, cidofovir, fomivirsen, foscarnet, ganciclovir, penciclovir, amantadine, rimantadine and zanamivir.

* * * * *